United States Patent
Romo et al.

(10) Patent No.: US 10,870,662 B2
(45) Date of Patent: *Dec. 22, 2020

(54) ALPHA-AMINO PATEAMINE A DERIVATIVES AND METHODS FOR TREATING CHRONIC LYMPHOCYTIC LEUKEMIA

(71) Applicant: The Texas A&M University System, College Station, TX (US)

(72) Inventors: Daniel Romo, Waco, TX (US); Ken Hull, Waco, TX (US); Mingzhao Zhu, Waco, TX (US); Omar Robles, Waco, TX (US)

(73) Assignee: The Texas A&M University System, College Station, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/555,741

(22) Filed: Aug. 29, 2019

(65) Prior Publication Data

US 2019/0382417 A1 Dec. 19, 2019

Related U.S. Application Data

(63) Continuation of application No. 15/563,891, filed as application No. PCT/US2016/025355 on Mar. 31, 2016, now Pat. No. 10,407,444.

(60) Provisional application No. 62/140,987, filed on Mar. 31, 2015.

(51) Int. Cl.
*C07D 513/08* (2006.01)
*A61K 47/68* (2017.01)

(52) U.S. Cl.
CPC ........ *C07D 513/08* (2013.01); *A61K 47/6803* (2017.08); *A61K 47/6867* (2017.08)

(58) Field of Classification Search
CPC .................................................. C07D 513/08
See application file for complete search history.

(56) References Cited

U.S. PATENT DOCUMENTS

| 7,230,021 | B2 | 6/2007 | Romo et al. |
| 8,841,285 | B2 | 9/2014 | Romo et al. |
| 10,407,444 | B2 * | 9/2019 | Romo ............... A61K 47/6803 |
| 2003/0216436 | A1 | 11/2003 | Romo et al. |
| 2013/0053994 | A1 | 2/2013 | Rensch et al. |

FOREIGN PATENT DOCUMENTS

| EP | 0647645 A1 | 4/1995 |
| WO | 2013152299 A2 | 10/2013 |

OTHER PUBLICATIONS

International Search Report and Written Opinion dated Jun. 20, 2016, issued in corresponding International Application No. PCT/US16/25355, filed Mar. 31, 2016, 10 pages.
International Search Report and Written Opinion dated Jun. 22, 2017, issued in related International Application No. PCT/US2017/025448, filed Mar. 31, 2017, 7 pages.
International Preliminary Report on Patentability dated Oct. 3, 2017, issued in corresponding International Application No. PCT/US2016/025355, filed Mar. 31, 2016, 8 pages.

* cited by examiner

*Primary Examiner* — Noble E Jarrell
(74) *Attorney, Agent, or Firm* — Christensen O'Connor Johnson Kindness PLLC

(57) ABSTRACT

Pateamine A derivatives and pharmaceutical compositions that include the derivatives. The pateamine A derivatives are α-amino pateamine A derivatives that lack the C5-methyl group of pateamine A.

21 Claims, 5 Drawing Sheets

ALPHA-AMINO PATEAMINE A DERIVATIVES AND METHODS FOR TREATING CHRONIC LYMPHOCYTIC LEUKEMIA

CROSS-REFERENCE TO RELATED APPLICATION

This application is a continuation of U.S. application Ser. No. 15/563,891, filed Oct. 2, 2017, now U.S. Pat. No. 10,407,444, which is the national stage of International Application No. PCT/US2016/025355, filed Mar. 31, 2016, which claims the benefit of Application No. 62/140,987, filed Mar. 31, 2015. Each application is expressly incorporated herein by reference in its entirety.

FIELD OF THE INVENTION

The present invention relates to α-amino pateamine A derivatives and methods for treating chronic lymphocytic leukemia using the α-amino pateamine A derivatives.

BACKGROUND OF THE INVENTION

Effective new cancer therapies have been developed based on agents with novel mechanisms of action that specifically target the pathophysiology of malignances. Most of these diseases exhibit a pronounced defect in normal lymphocyte cell death mechanisms due to over-expression of pro-survival proteins. It is now recognized that a critical aspect of B cell malignancy metabolism is directed at replenishing the pro-survival proteins that keep these cells from dying due to apoptosis. This is required because sequence motifs intrinsic to the primary protein structure of these pro-survival proteins, signal for the rapid turnover of these proteins (e.g. Mcl-1, XIAP). This is a hallmark of the pathophysiology of B cell malignancies. Importantly, even transient inhibition of translation rapidly diminishes these key proteins to a level that cannot prevent apoptosis. Once initiated, this lethal process is irreversible. Because normal lymphoid cells do not exhibit this dependency, it appears that CLL cells are "addicted" to the continual expression of the anti-apoptotic proteins for survival.

Pateamine A (PatA) was initially isolated from the marine sponge *Mycale* sp. by bioassay-guided fractionation based on its cytotoxic activity against P388 murine leukemia cells ($IC_{50}$, 0.27 nmol/L). Consistent with its cytotoxicity, PatA was subsequently shown to induce apoptosis in several cancer cell lines. Des-methyl, des-amino pateamine A (DMDAPatA) is a simplified analog of the natural product that is easier to synthesize and a potent anti-proliferative agent in vitro against >30 human cancer cell lines.

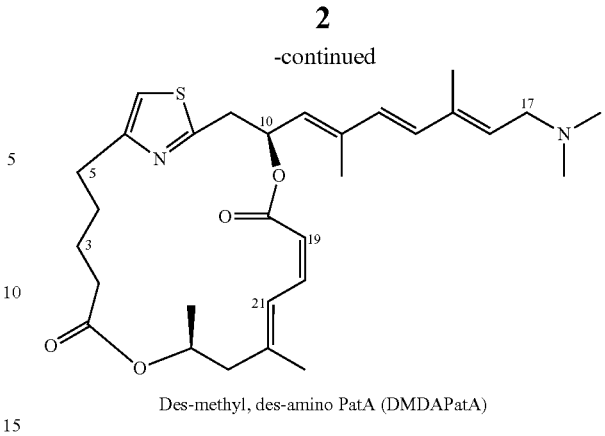

Des-methyl, des-amino PatA (DMDAPatA)

PatA and DMDAPatA inhibit cap-dependent translation initiation by sequestration of eIF4A that prevents formation of the eIF4F complex, or by stalling the initiation complex on mRNA. Xenograft studies in mice showed DMDAPatA has high activity in models of human leukemia and melanoma leading to significant tumor reduction, thus demonstrating good bioavailability. The synthesis of >20 derivatives of PatA led to the identification of DMDAPatA which was also found to be significantly more stable than the natural product. Overexpression of multidrug resistant protein did not affect this activity. Importantly, DMDAPatA reduces the levels of intrinsically short-lived anti-apoptotic proteins in primary CLL cells, and initiates apoptosis. However, preliminary data on DMDAPatA suggests that it is highly protein bound in human plasma and may lack sufficient in vivo potency required for development as an effective therapeutic agent.

Although PatA and DMDAPatA appear to be attractive candidates for the development of therapeutic agents, a need exists for improved PatA derivatives having therapeutic effectiveness, low toxicity, and advantageous pharmacokinetic properties.

The present invention seeks to fulfill these needs and provides further related advantages.

SUMMARY OF THE INVENTION

The present invention provides α-amino pateamine A derivatives, pharmaceutical compositions that include the derivatives, an methods for using the derivatives.

In one aspect, the invention provides α-amino pateamine A derivatives.

In one embodiment, the invention provides pateamine A derivatives having formula (I), stereoisomers, racemates, and pharmaceutically salts thereof:

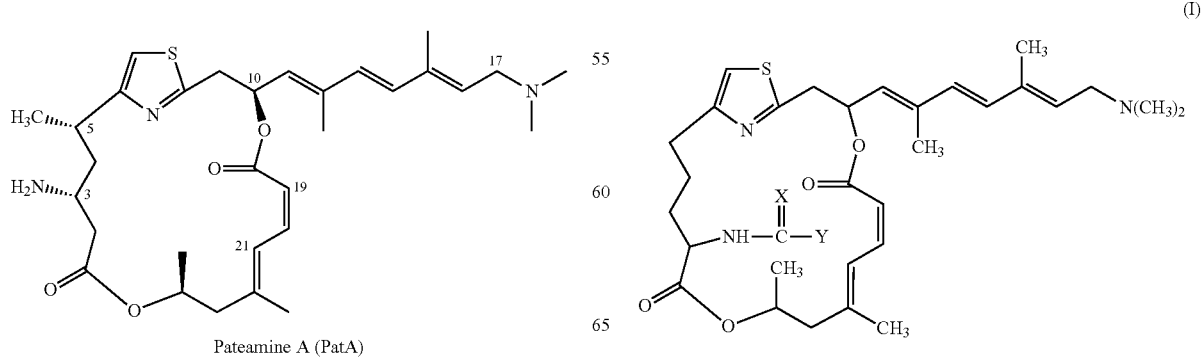

wherein

X is selected from O, NH, and S; and

Y is selected from R, OR, SR, and N(R$^1$)R$^2$, wherein R is selected from C1-C6 alkyl, C1-C6 haloalkyl, C6-C10 aryl, and C3-C12 alkyl groups in which one or more carbons are replaced with O or N atoms, and wherein R$^1$ and R$^2$ are independently selected from hydrogen, C1-C6 alkyl, C1-C6 haloalkyl, C6-C10 aryl, and C3-C12 alkyl groups in which one or more carbons are replaced with O or N atoms.

In certain embodiments, the invention provides pateamine A derivatives having formula (IIA) and pharmaceutically salts thereof:

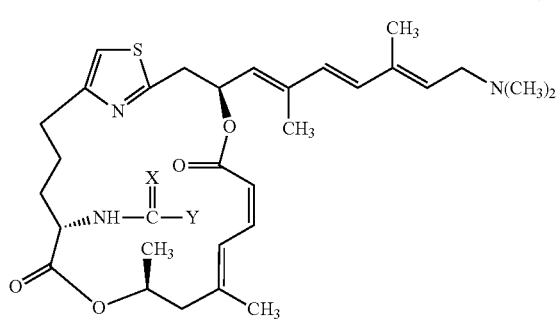

(IIA)

wherein X, Y, R, R$^1$, and R$^2$ are as above for formula (I).

In other embodiments, the invention provides pateamine A derivatives having formula (IIB) and pharmaceutically salts thereof:

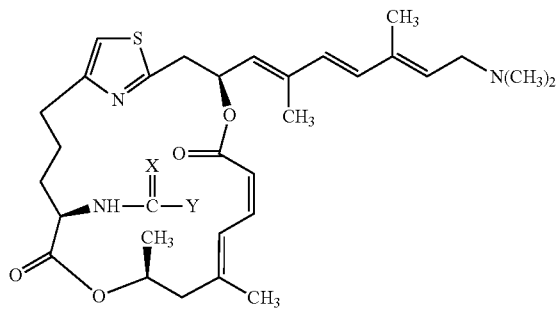

(IIB)

wherein X, Y, R, R$^1$, and R$^2$ are as above for formula (I).

Representative salts of the invention have formula (III):

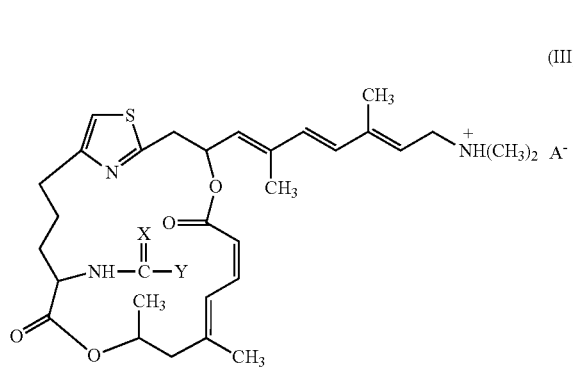

(III)

wherein X and Y are as described above for formulae (I) and (II), and A$^-$ is a pharmaceutically acceptable counter ion.

In certain embodiments, representative salts of the invention have formula (IVA):

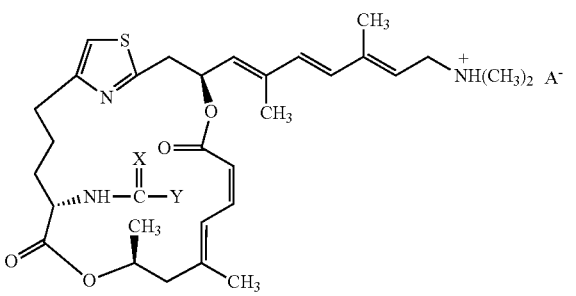

(IVA)

wherein X and Y are as described above for formulae (I) and (II), and A$^-$ is a pharmaceutically acceptable counter ion.

In other embodiments, representative salts of the invention have formula (IVB):

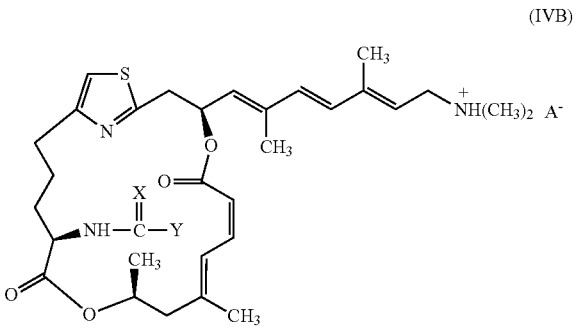

(IVB)

wherein X and Y are as described above for formulae (I) and (II), and A$^-$ is a pharmaceutically acceptable counter ion.

In another embodiment, the invention provides pateamine A derivatives having formula (V), stereoisomers, racemates, and pharmaceutically salts thereof:

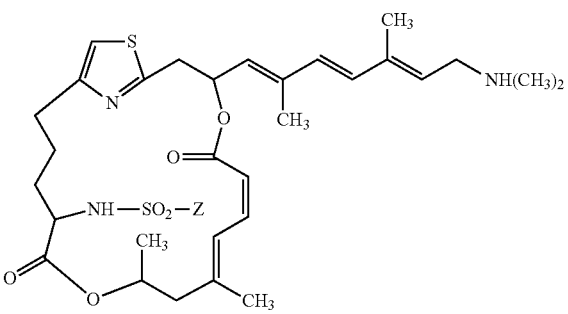

(V)

wherein

Z is selected from R and OR$^1$, wherein R and R$^1$ are as described above for formulae (I)-(IV).

In certain embodiments, the invention provides pateamine A derivatives having formula (VIA) and pharmaceutically salts thereof:

(VIA)

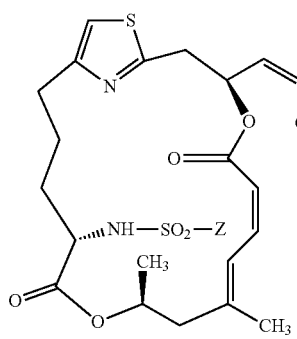

wherein Z is as described above for formula (V).

In other embodiments, the invention provides pateamine A derivatives having formula (VIB) and pharmaceutically salts thereof:

(VIB)

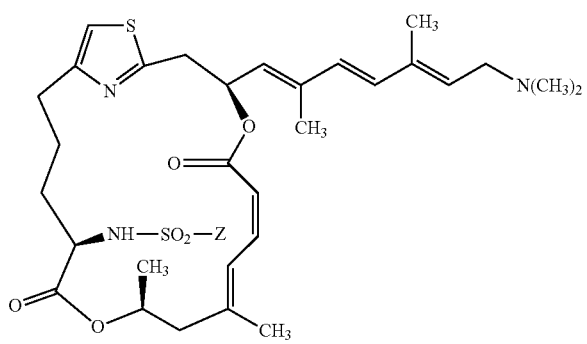

wherein Z is as described above for formula (V).

Representative salts of the invention have formula (VII):

(VII)

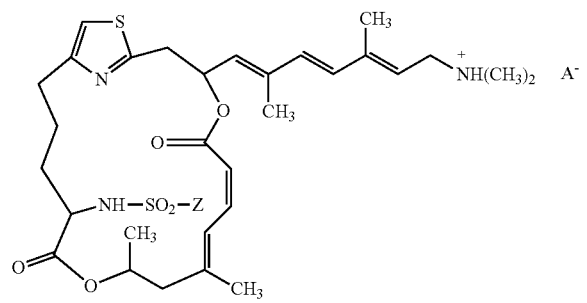

wherein Z is as described above for formulae (V) and A⁻ is a pharmaceutically acceptable counter ion.

In certain embodiments, representative salts of the invention have formula (VIIIA):

(VIIIA)

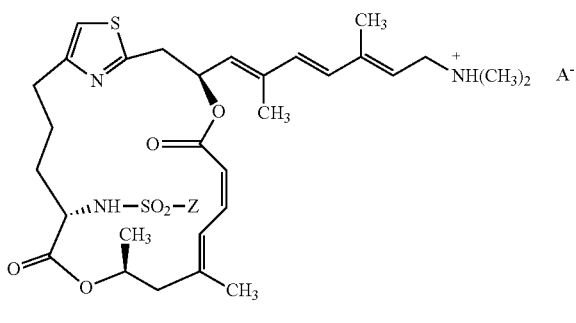

wherein Z is as described above for formula (V) and A⁻ is as described above for formula (VII).

In other embodiments, representative salts of the invention have formula (VIIIB):

(VIIIB)

wherein Z is as described above for formula (V) and A⁻ is as described above for formula (VII).

In another aspect, the invention provides antibody drug conjugates for the delivery of the α-amino pateamine derivatives of the invention.

In a further aspect, the invention provides pharmaceutical compositions that include a compound of the invention (i.e., a compounds of formulae (I), (II), (III), (IV), (V), (VI), (VII), or (VIII)) and a pharmaceutically acceptable carrier. The invention also provides pharmaceutical compositions that include an antibody conjugate of the invention (i.e., an antibody conjugate that delivers a compound of formulae (I), (II), (III), (IV), (V), (VI), (VII), or (VIII)) and a pharmaceutically acceptable carrier.

In another aspect, the invention provides a method for inhibiting growth of chronic lymphocytic leukemia (CLL) cells. In the method, growth of CLL cells is inhibited by contacting CLL cells with an α-amino pateamine compound of the invention. In certain embodiments, the method is effective for inhibiting growth of chronic lymphocytic leukemia (CLL) cells in a subject (e.g., a human subject).

In a further aspect, the invention provides a method for treating chronic lymphocytic leukemia (CLL). In the method, CLL is treated by administering an effective amount of an α-amino pateamine compound of the invention to a subject (e.g., a human subject) in need thereof.

DESCRIPTION OF THE DRAWINGS

The foregoing aspects and many of the attendant advantages of this invention will become more readily appreciated as the same become better understood by reference to the following detailed description, when taken in conjunction with the accompanying drawings.

DETAILED DESCRIPTION OF THE INVENTION

Figures 1A, 1B:
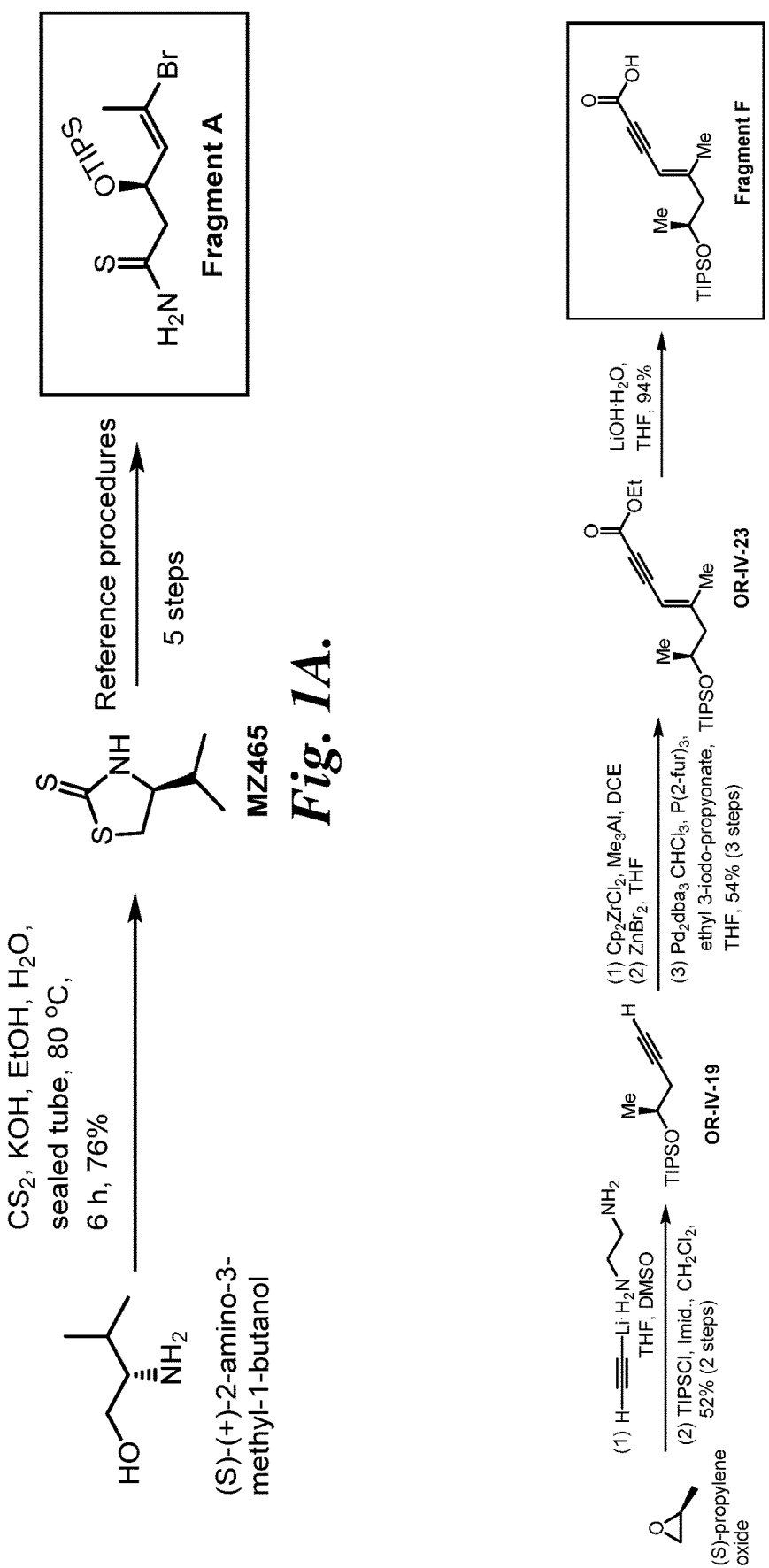
FIGS. 1A-1D are schematic illustrations showing the preparation of a representative α-amino pateamine A derivative of the invention (MZ579).

The present invention provides α-amino pateamine A derivatives, pharmaceutical compositions that include the derivatives, an methods for using the derivatives.

The compounds of the invention are simplified analogs of pateamine A that lack the C5-methyl group. The compounds of the invention are α-amino (2-amino) pateamine A derivatives.

The compounds of the invention are derivatives of the translation inhibitor pateamine A and as pateamine A derivatives, the compounds of the invention are expected to provide anticancer and antiproliferative effects by inhibition of eIF4A-dependent translation initiation.

The compounds of the invention display potent inhibitory activity against chronic lymphocytic leukemia (CLL) cells and lower plasma protein binding (PPB) in human plasma. The combination of potency and low PPB render the compounds candidates for development of therapeutic agents for treatment of CLL.

The inhibition of translation in CLL cells has the potential for clinical development of therapies for B cell malignancies and to overcome drug resistance to existing standard of care therapeutics. Relapsed refractory CLL remains a clinical problem associated with poor overall survival. Due to their unique mode of action, inhibition of translation and protein biosynthesis, the compounds of the invention may be useful for combating resistant forms of CLL.

α-Amino Pateamine Derivatives

In one embodiment, the invention provides pateamine A derivatives having formula (I), stereoisomers, racemates, and pharmaceutically salts thereof:

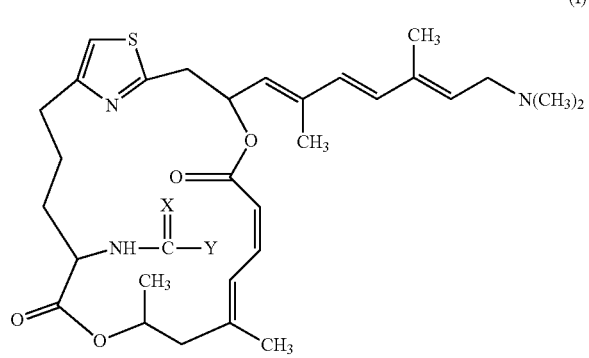

(I)

wherein

X is selected from O, NH, and S; and

Y is selected from R, $OR^1$, $SR^1$, and $N(R^1)R^2$, wherein R is selected from C1-C6 alkyl, C1-C6 haloalkyl, C6-C10 aryl, and C3-C12 alkyl groups in which one or more carbons are replaced with O or N atoms, and wherein $R^1$ and $R^2$ are independently selected from hydrogen, C1-C6 alkyl, C1-C6 haloalkyl, C6-C10 aryl, and C3-C12 alkyl groups in which one or more carbons are replaced with O or N atoms.

In certain embodiments, the invention provides pateamine A derivatives having formula (IIA) and pharmaceutically salts thereof:

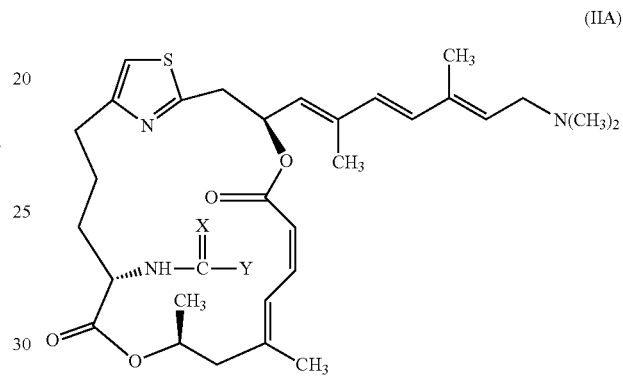

(IIA)

wherein X, Y, R, $R^1$, and $R^2$ are as above for formula (I).

In other embodiments, the invention provides pateamine A derivatives having formula (IIB) and pharmaceutically salts thereof:

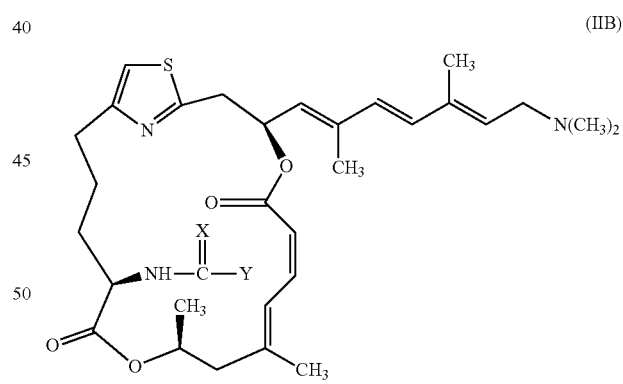

(IIB)

wherein X, Y, R, $R^1$, and $R^2$ are as above for formula (I).

Pharmaceutically acceptable salts may be formed from compounds of formulae (I) and (II) and a pharmaceutically acceptable organic acids (e.g., carboxylic acids) or inorganic acid (e.g., mineral acids). Representative acids include hydrochloric acid, sulfuric acid, phosphoric acid, formic acid, acetic acid, trifluoroacetic acid, maleic acid, fumaric acid, succinic acid, tartaric acid, oxalic acid, citric acid, malic acid, benzoic acid, toluenesulfonic acid, methanesulfonic acid, and benzenesulfonic acid. Such salts may be formed during or after the synthesis of the compounds of formulae (I) or (II).

Representative salts of the invention have formula (III):

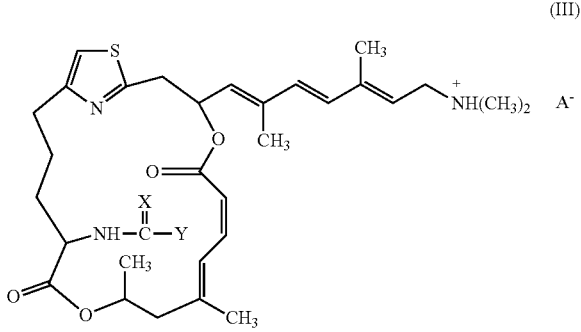

(III)

wherein X and Y are as described above for formulae (I) and (II), and A⁻ is a pharmaceutically acceptable counter ion. Suitable counter ions include chloride, bromide, iodide, sulfate, phosphate, formate, acetate, trifluoroacetate, maleate, fumarate, succinate, tartrate, oxalate, citrate, malate, benzoate, toluenesulfonate, methanesulfonate, and benzenesulfonate.

In certain embodiments, representative salts of the invention have formula (IVA):

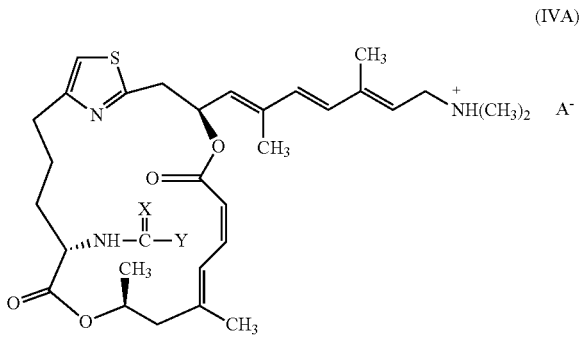

(IVA)

wherein X and Y are as described above for formulae (I) and (II), and A⁻ is a pharmaceutically acceptable counter ion.

In other embodiments, representative salts of the invention have formula (IVB):

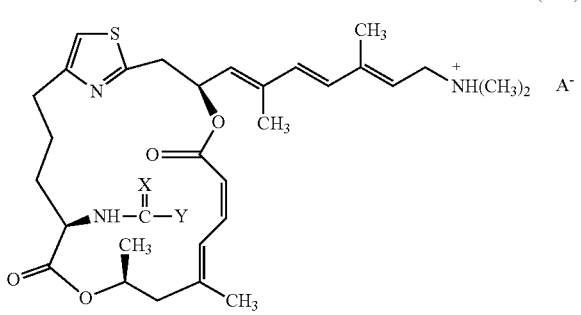

(IVB)

wherein X and Y are as described above for formulae (I) and (II), and A⁻ is a pharmaceutically acceptable counter ion.

Suitable counter ions include chloride, bromide, iodide, sulfate, phosphate, formate, acetate, trifluoroacetate, maleate, fumarate, succinate, tartrate, oxalate, citrate, malate, benzoate, toluenesulfonate, methanesulfonate, and benzenesulfonate.

For compounds of formulae (I), (II), (III), and (IV), C1-C6 alkyl groups include straight chain (i.e., methyl, ethyl, n-propyl, n-butyl, n-pentyl, and n-hexyl), branched (e.g., s-propyl, s-butyl, t-butyl, s-pentyl, and s-hexyl), and cycloalkyl (i.e., cyclopropyl, cyclobutyl, cyclopentyl, and cyclohexyl) group;

C1-C6 haloalkyl groups include C1-C6 alkyl groups further substituted with one or more halo (e.g., fluoro or chloro) groups (e.g., trifluoromethyl or trichloromethyl);

C6-C10 aryl groups include phenyl groups optionally substituted with one of more alkyl groups (e.g., methyl, ethyl);

C3-C12 alkyl groups refer to C3-C12 alkyl groups in which one or more carbons are replaced with O or N atoms include ether-containing groups and amine-containing groups that may impart increased water solubility to the compounds. Representative ether-containing groups include —$CH_2$—O—$CH_3$, —$CH_2CH_2$—O—$CH_3$, and —$CH_2CH_2$—O—$CH_2CH_2$—O—$CH_3$. Representative amine-containing groups include —$CH_2$—NH—$CH_3$, —$CH_2$—N($CH_3$)$_2$, —$CH_2CH_2$—NH—$CH_3$, and —$CH_2CH_2$—N($CH_3$)$_2$.

The invention provides compounds of formulae (I), (IIA), (IIB), (III), (IVA) and (IVB) including the following embodiments:

X is O and Y is R (amides), in certain of these embodiments, R is methyl, trifluoromethyl, or t-butyl;

X is O and Y is OR¹ (carbamates), in certain of these embodiments, R¹ is methyl or t-butyl;

X is O and Y is N(R¹)R² (ureas), in certain of these embodiments, R¹ is hydrogen and R² is hydrogen, or R¹ is hydrogen and R² is methyl;

X is O and Y is SR¹, in certain of these embodiments, R¹ is methyl or t-butyl;

X is S and Y is R (thioamides), in certain of these embodiments, R is methyl;

X is S and Y is OR¹ (thiocarbamates), in certain of these embodiments, R¹ is methyl or t-butyl;

X is S and Y is N(R¹)R² (thioureas), in certain of these embodiments, R¹ is hydrogen and R² is hydrogen, or R¹ is hydrogen and R² is methyl;

X is S and Y is SR¹, in certain of these embodiments, R¹ is methyl or t-butyl;

X is NH and Y is R, in certain of these embodiments, R is methyl, trifluoromethyl, or t-butyl;

X is NH and Y is OR¹, in certain of these embodiments, R¹ is methyl or t-butyl;

X is NH and Y is N(R¹)R², in certain of these embodiments, R¹ is hydrogen and R² is hydrogen, or R¹ is hydrogen and R² is methyl; and X is NH and Y is SR¹, in certain of these embodiments, R¹ is methyl or t-butyl.

Figure 1C:
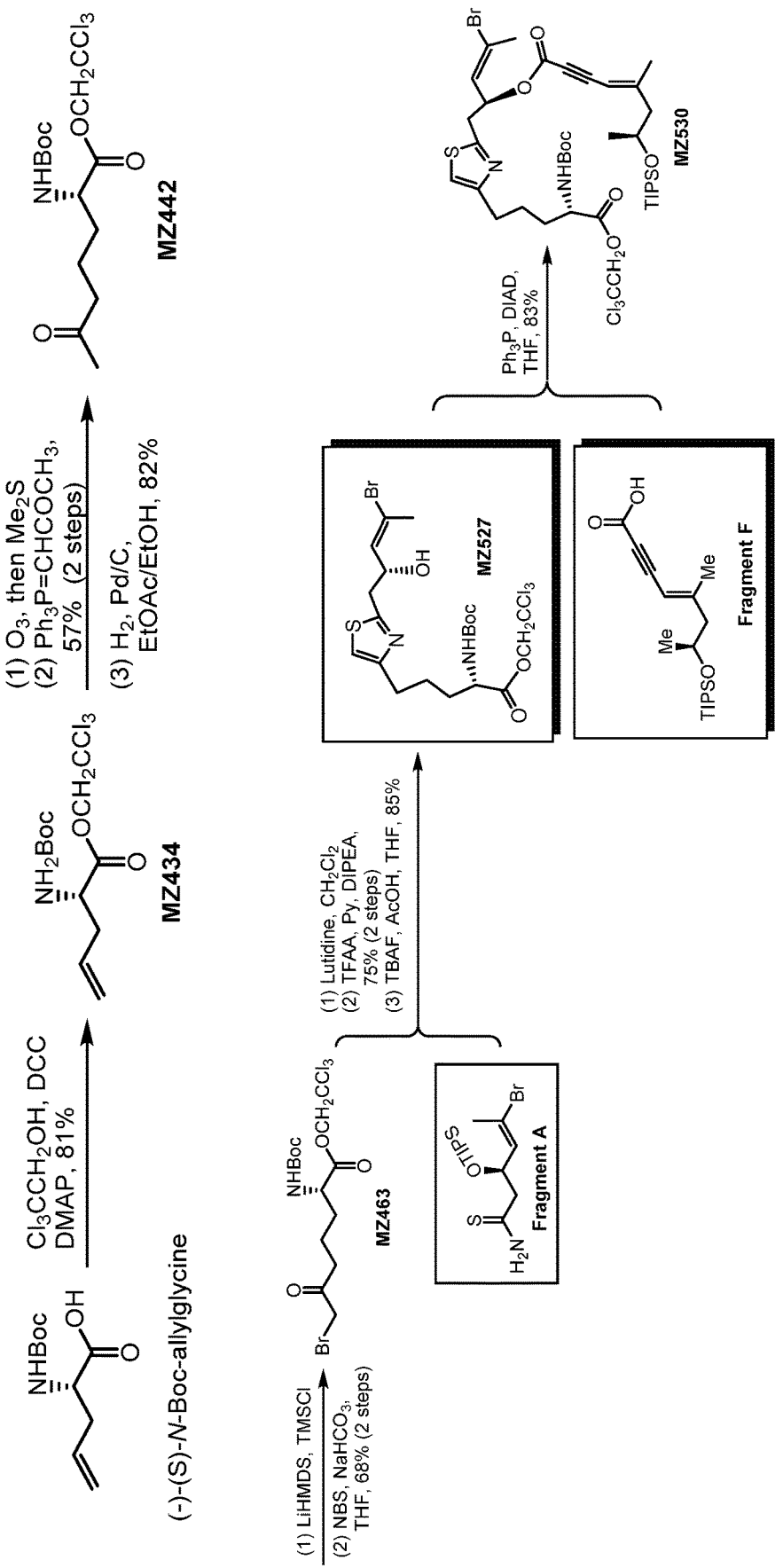
Figure 1D:
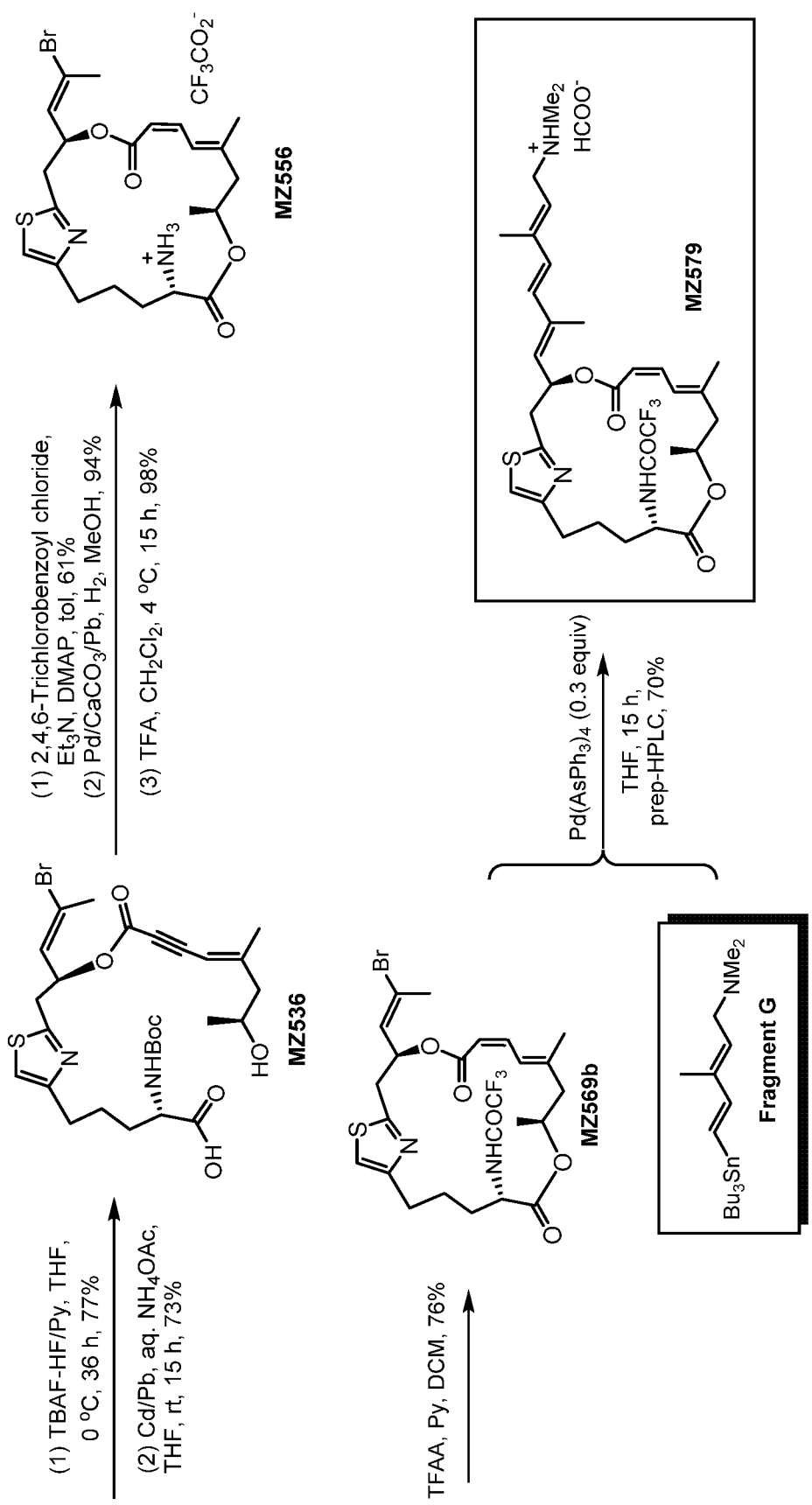
Figure 2A:
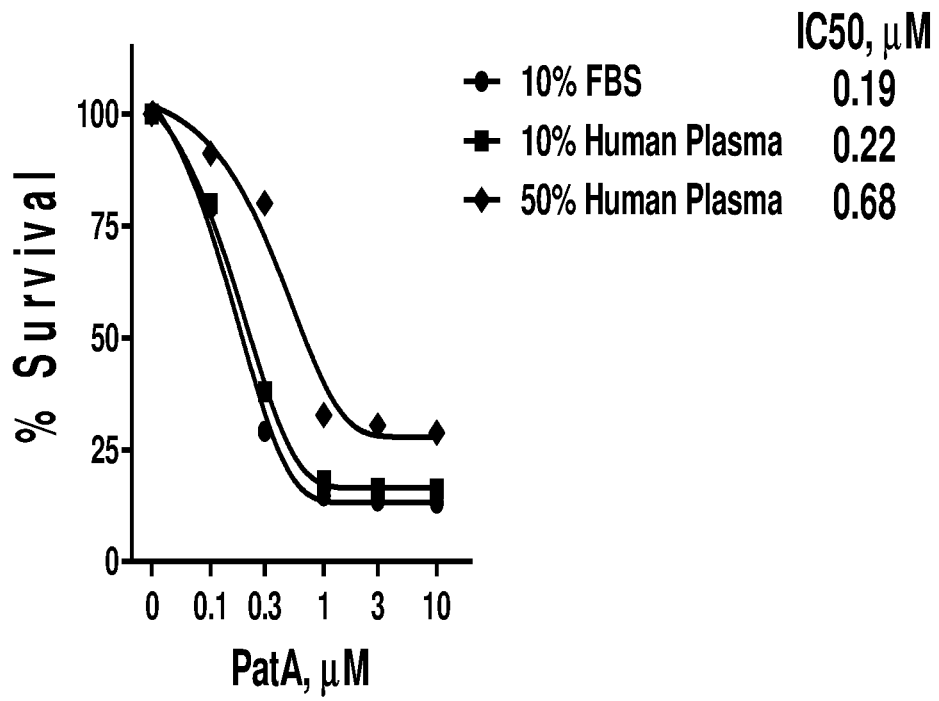
FIGS. 2A-2D compare $IC_{50}$ dose response curves (% survival of chronic lymphocytic leukemia (CLL) cells as a function of agent concentration (μM)) for pateamine A (PatA) (2A), desmethyl desamino pateamine A (DM-DAPatA) (2B), α-amino pateamine A derivative (MZ578) (2C), and α-amino pateamine A derivative (MZ579) (2D) in 10% fetal bovine serum (FBS), 10% human plasma, and 50% human plasma.
Figure 2B:
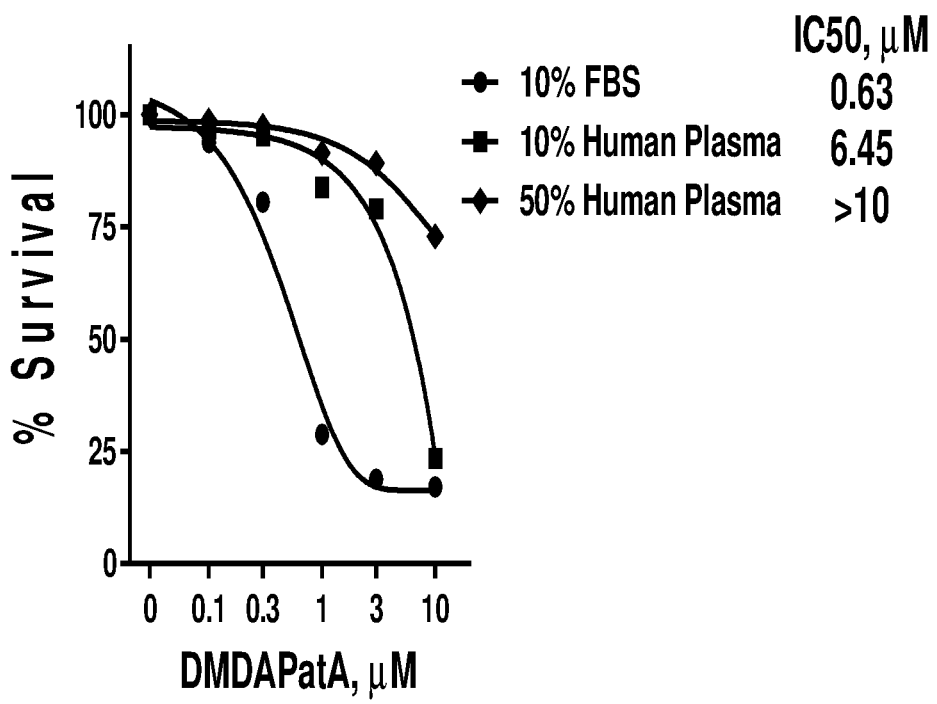
Figure 2C:
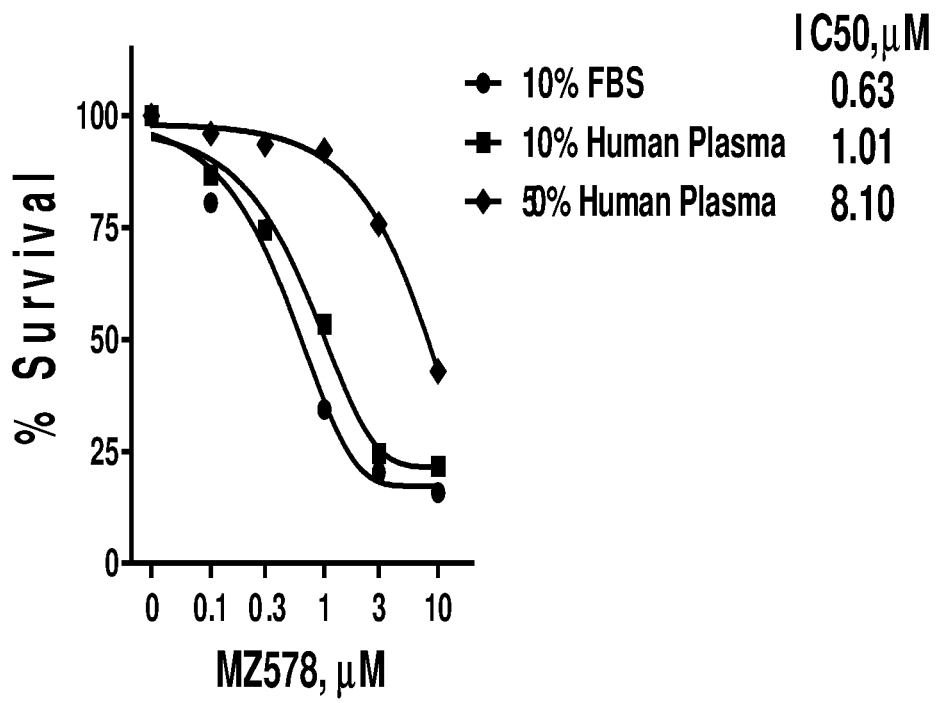
Figure 2D:
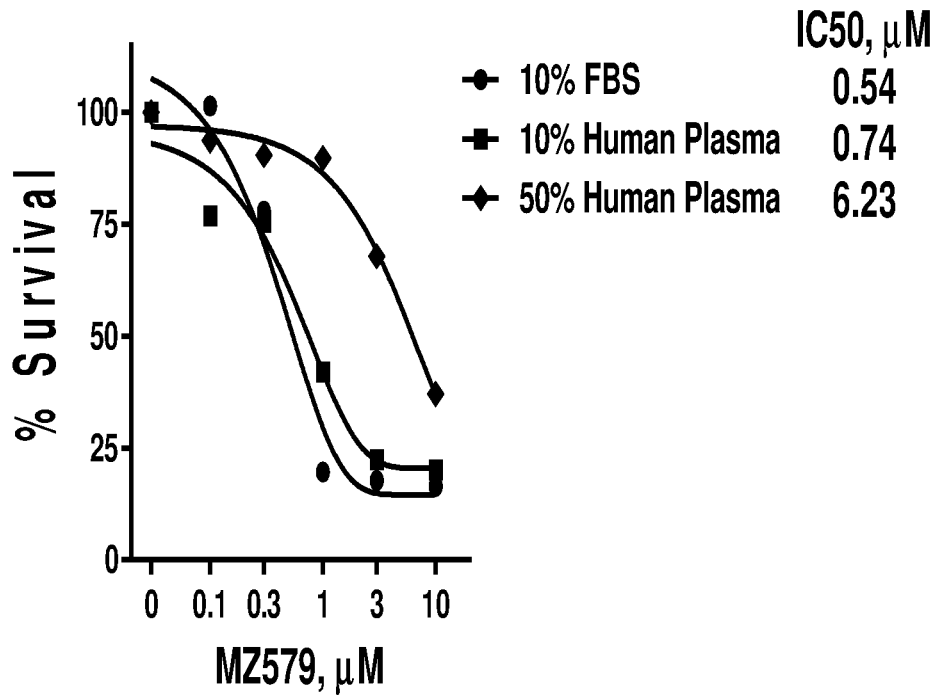

The preparation of a representative α-amino pateamine A amide derivative of the invention is described in Example 1 and illustrated in FIG. 1 (MZ579).

The preparation of another representative pateamine A amide derivative of the invention (MZ623) is described in Example 2.

The preparation of a further representative pateamine A amide derivative of the invention (MZ757) is described in Example 5.

The preparation of a representative pateamine A carbamate derivative of the invention (MZ578) is described in Example 3.

The preparation of a another representative pateamine A carbamate derivative of the invention (MZ756) is described in Example 5.

In another embodiment, the invention provides pateamine A derivatives having formula (V), stereoisomers, racemates, and pharmaceutically salts thereof:

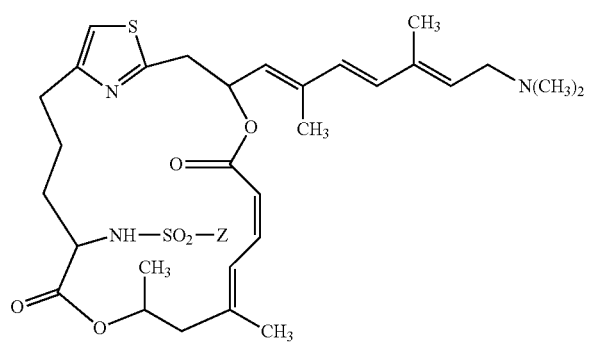

(V)

wherein
Z is selected from R and OR¹, wherein R and R¹ are as described above for formulae (I)-(IV).

In certain embodiments, the invention provides pateamine A derivatives having formula (VIA) and pharmaceutically salts thereof:

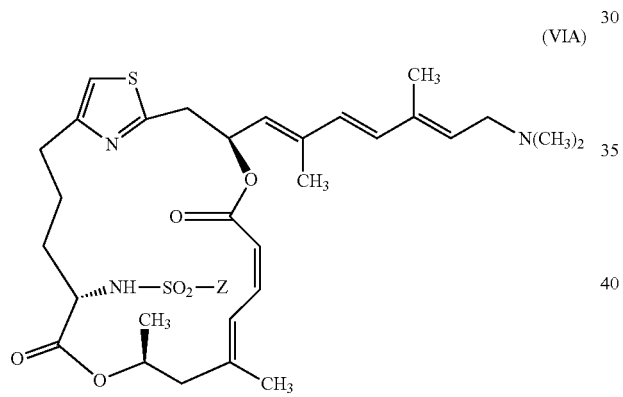

(VIA)

wherein Z is as described above for formula (V).

In other embodiments, the invention provides pateamine A derivatives having formula (VIB) and pharmaceutically salts thereof:

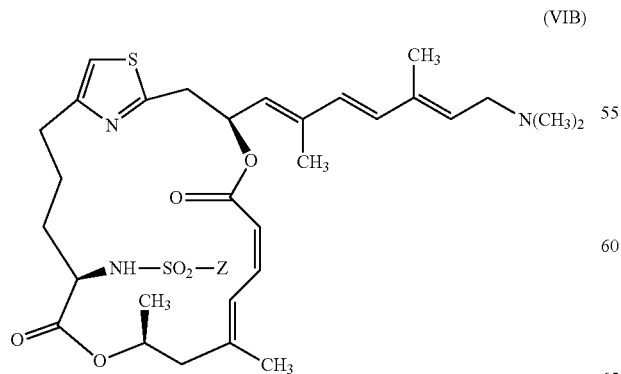

(VIB)

wherein Z is as described above for formula (V).

Representative salts of the invention have formula (VII):

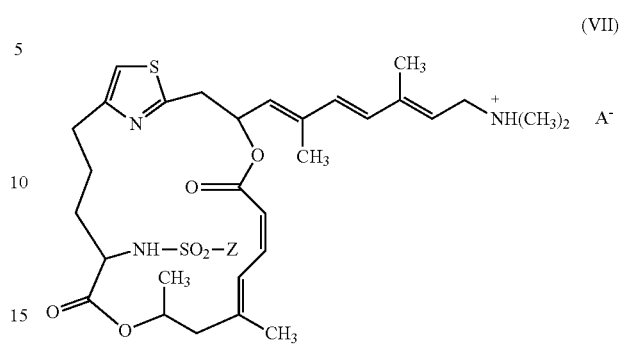

(VII)

wherein Z is as described above for formulae (V) and A⁻ is a pharmaceutically acceptable counter ion. Suitable counter ions include chloride, bromide, iodide, sulfate, phosphate, formate, acetate, trifluoroacetate, maleate, fumarate, succinate, tartrate, oxalate, citrate, malate, benzoate, toluenesulfonate, methanesulfonate, and benzenesulfonate.

In certain embodiments, representative salts of the invention have formula (VIIIA):

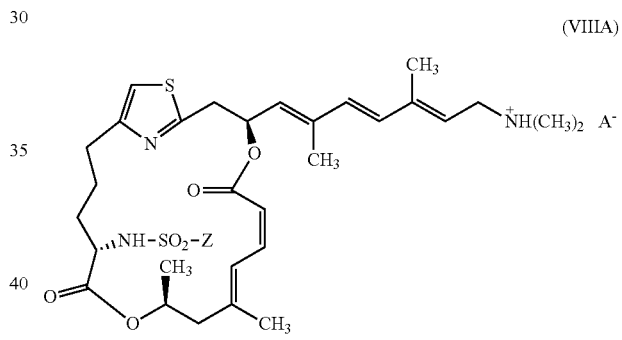

(VIIIA)

wherein Z is as described above for formula (V) and A⁻ is as described above for formula (VII).

In other embodiments, representative salts of the invention have formula (VIIIB):

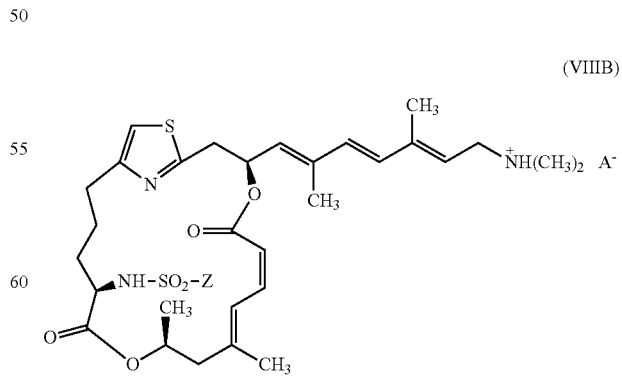

(VIIIB)

wherein Z is as described above for formula (V) and A⁻ is as described above for formula (VII).

The invention provides compounds of formulae (V), (VIA), (VIB), (VII), (VIIIA), and (VIIIB) including the following embodiments:

Z is C1-C6 alkyl (e.g., methyl);

Z is C1-C6 haloalkyl (e.g., trifluoromethyl);

Z is C6-C10 aryl (e.g., phenyl); and

Z is C3-C12 alkyl in which one or more carbons are replaced with O or N atoms (e.g., —CH$_2$—O—CH$_3$, —CH$_2$CH$_2$—O—CH$_3$, and —CH$_2$CH$_2$—O—CH$_2$CH$_2$—O—CH$_3$, or —CH$_2$—NH—CH$_3$, —CH$_2$—N(CH$_3$)$_2$, —CH$_2$CH$_2$—NH—CH$_3$, and —CH$_2$CH$_2$—N(CH$_3$)$_2$).

The α-amino pateamine derivatives of the invention (i.e. compounds of formulae (I)-(VIII)) can be prepared by reacting the 2-amino group (i.e., α-amino group) of the macrocycle with a suitably reactive reagent (e.g., N-acylating or N-sulfonating reagent) to provide a variety of α-amino pateamine derivatives.

The preparation of a representative pateamine A sulfonamide derivative of the invention (MZ624) is described in Example 4.

Antibody Conjugates

In another aspect, the invention provides antibody drug conjugates for the delivery of the α-amino pateamine derivatives of the invention. The antibody drug conjugates are readily prepared from the α-amino pateamine derivatives by conjugation chemistry known in the art. In certain embodiments, the α-amino pateamine derivatives are conjugated to the antibody through the 2-amino group (i.e., α-amino group).

In certain embodiments, the antibody drug conjugate is an Antibody-Linker-Drug conjugate of the formula: Ab-(LU-D)$_p$ or a pharmaceutically acceptable salt or solvate thereof wherein, Ab is an antibody unit, LU is a linker unit, D is a drug unit, and p is an integer from 1 to about 20. For the antibody drug conjugates, D includes a β-amino pateamine derivative of the invention.

Suitable antibodies include, for example, monoclonal antibodies, such as chimeric, humanized or human antibodies or an antigen-binding fragment thereof. In some embodiments, the antibody unit comprises an antigen-binding region that binds to a target antigen.

In some embodiments, a substantial amount of the drug unit is not cleaved from the conjugate until the conjugate enters a cell with a cell-surface receptor specific for the antibody unit, and the drug unit is cleaved from the antibody unit when the conjugate enters the cell. In some embodiments, a substantial amount of the linker-drug unit is not cleaved from the conjugate until the conjugate enters a cell with a cell-surface receptor specific for the antibody unit, and the linker-drug unit is cleaved from the antibody unit when the conjugate enters the cell.

The term "antibody" as used herein, refers to a full-length immunoglobulin molecule or an immunologically active portion of a full-length immunoglobulin molecule (i.e., a molecule that contains an antigen binding site that immunospecifically binds an antigen of a target of interest or part thereof, such targets including, but not limited to, cancer cells. The antibody can be of any class (e.g., IgG, IgE, IgM, IgD, and IgA), or subclass (e.g., IgG1, IgG2, IgG3, IgG4, IgA1, and IgA2) of immunoglobulin molecule.

The antibody can be derived from any species. In one aspect, the antibody is of human, murine, or rabbit origin. In another aspect, the antibody is polyclonal, monoclonal, bispecific, multispecific, human, humanized or a chimeric antibody, or an epitope-binding fragment of any of the above which immunospecifically bind to a target antigen.

The term "monoclonal antibody" as used herein refers to an antibody obtained from a population of substantially homogeneous antibodies (i.e., the individual antibodies comprising the population are identical except for possible naturally-occurring mutations that may be present in minor amounts). Monoclonal antibodies are highly specific, being directed against a single antigenic site.

Monoclonal antibodies specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, that exhibit the desired biological activity. For example, a chimeric antibody may be derived from the variable region from a mouse antibody and the constant region from a human antibody.

An "antibody fragment" refers to a portion of an intact antibody, typically comprising the antigen-binding or variable region thereof. Examples of antibody fragments include Fab, Fab', F(ab')2, and Fv fragments; linear antibodies; single-chain antibody molecules; an scFv; an IgG ΔCH2, a minibody, a diabody, a triabody, a tetrabody, a dsFv; an sc-Fv-Fc; an (scFv)2; a fragment produced by a Fab expression library; an anti-idiotypic (anti-Id) antibody; and multispecific antibodies formed from antibody fragment(s).

An "intact" antibody is one which comprises an antigen-binding variable region as well as a light chain constant domain (CO and heavy chain constant domains, CH1, CH2 and CH3. The constant domains may be native sequence constant domains (e.g., human native sequence constant domains) or amino acid sequence variants thereof.

The term "diabodies" refers to small antibody fragments with two antigen-binding sites, which fragments comprise a variable heavy domain (VH) connected to a variable light domain (VL) in the same polypeptide chain. By using a linker that is too short to allow pairing between the two domains on the same chain, the domains are forced to pair with the complementary domains of another chain and create two antigen-binding sites. "Humanized" forms of non-human (e.g., rodent) antibodies are chimeric antibodies that contain minimal sequence derived from non-human immunoglobulin. For the most part, humanized antibodies are human immunoglobulins (recipient antibody) in which residues from a hypervariable region of the recipient are replaced by residues from a hypervariable region of a non-human species (donor antibody) such as mouse, rat, rabbit or non-human primate having the desired specificity, affinity, and capacity. In some instances, framework region (FR) residues of the human immunoglobulin are replaced by corresponding non-human residues. Furthermore, humanized antibodies may comprise residues that are not found in the recipient antibody or in the donor antibody.

These modifications are made to further refine antibody performance. In general, the humanized antibody will comprise substantially all of at least one, and typically two, variable domains in which all or substantially all of the hypervariable loops correspond to those of a non-human immunoglobulin and all or substantially all of the FRs are those of a human immunoglobulin sequence. The humanized antibody optionally also will comprise at least a portion of an immunoglobulin constant region (Fc), typically that of a human immunoglobulin.

Useful monoclonal antibodies include, but are not limited to, human monoclonal antibodies, humanized monoclonal antibodies, antibody fragments, or chimeric (e.g., human-mouse or other species) monoclonal antibodies. Human monoclonal antibodies may be made by any of numerous techniques known in the art.

The antibody can also be a multispecific antibody, such as a bispecific antibody. Methods for making bispecific antibodies are known in the art. Traditional production of full-length bispecific antibodies is based on the coexpression of two immunoglobulin heavy chain-light chain pairs, where the two chains have different specificities. Because of the random assortment of immunoglobulin heavy and light chains, these hybridomas (quadromas) produce a potential mixture of 10 different antibody molecules.

Pharmaceutical Compositions

In another aspect, the invention provides pharmaceutical compositions that include a compound of the invention (i.e., a compounds of formulae (I), (II), (III), (IV), (V), (VI), (VII), or (VIII)) and a pharmaceutically acceptable carrier.

The invention also provides pharmaceutical compositions that include an antibody conjugate of the invention (i.e., an antibody conjugate that delivers a compound of formulae (I), (II), (III), (IV), (V), (VI), (VII), or (VIII)) and a pharmaceutically acceptable carrier.

Suitable carriers include those suitable for administration to an animal (e.g., a human subject). Pharmaceutical compositions suitable for injectable use include sterile aqueous solutions (e.g., saline, dextrose) and dispersions.

The compounds and compositions of the invention can be orally administered, for example, with an inert diluent or carrier, enclosed in hard or soft shell gelatin capsule, or compressed into tablets. For oral therapeutic administration, the compounds and compositions can be combined with excipients and used in the form of ingestible tablets, buccal tables, troches, capsules, elixirs, suspensions, syrups, wafers, and the like. The amount of active compounds in such therapeutically useful compositions is such that a suitable dosage is obtained.

The compounds and compositions of the invention can be administered parenterally or intraperitoneally. Solutions of the compounds as free base or pharmacologically acceptable salts can be prepared in water suitably mixed with additives, such as surfactants. Dispersions can also be prepared in in oils.

In the methods of the invention, the term "therapeutically effective amount" refers to an amount effective, at dosages and for periods of time necessary, to achieve the desired therapeutic result, such as reduced levels of rod gene expression or their protein products. A therapeutically effective amount of a compound may vary according to factors such as the disease state, age, sex, and weight of the subject, and the ability of the compound to elicit a desired response in the subject. Dosage regimens can be adjusted to provide the optimum therapeutic response. A therapeutically effective amount is also one in which any toxic or detrimental effects of the administered compound are outweighed by the therapeutically beneficial effects.

It is to be noted that dosage values can vary with the severity of the condition to be alleviated. For any particular subject, specific dosage regimens can be adjusted over time according to the individual need and the professional judgment of the person administering or supervising the administration of the compositions. Dosage ranges set forth herein are exemplary only and do not limit the dosage ranges that can be selected by a medical practitioner. The amount of active compound in the composition can vary according to factors such as the disease state, age, sex, and weight of the subject. Dosage regimens can be adjusted to provide the optimum therapeutic response. For example, a single bolus can be administered, several divided doses can be administered over time or the dose can be proportionally reduced or increased as indicated by the exigencies of the therapeutic situation.

In the methods, the administration of the compound can be systemic administration to the subject. The term "subject" is intended to include mammalian organisms. Examples of subjects include humans and non-human mammals. In specific embodiments of the invention, the subject is a human.

The terms "administering," "contacting," or "treating" include any method of delivery of a compounds or a pharmaceutical composition comprising the compound into a subject's system.

Methods of Use

In certain embodiments, the α-amino pateamine compounds of the invention retain the advantageous potency of pateamine A (e.g., inhibitory activity against chronic lymphocytic leukemia (CLL) cells) and have improved bioavailability compared to pateamine A (e.g., lower plasma protein binding (PPB) in human plasma).

In one aspect, the invention provides a method for inhibiting growth of chronic lymphocytic leukemia (CLL) cells. In the method, growth of CLL cells is inhibited by contacting CLL cells with an α-amino pateamine compound of the invention. In certain embodiments, the method is effective for inhibiting growth of chronic lymphocytic leukemia (CLL) cells in a subject (e.g., a human subject).

In another aspect, the invention provides a method for treating chronic lymphocytic leukemia (CLL). In the method, CLL is treated by administering an effective amount of an α-amino pateamine compound of the invention to a subject (e.g., a human subject) in need thereof.

Biological Activity of 2-Amino Pateamine Derivatives

Peripheral blood from the CLL patients were collected in heparin vacutainer tubes and centrifuged at 1500 rpm for 15 min to separate the plasma. The plasma (upper layer) was removed and saved for cell culture. The lower layer was diluted with phosphate-buffered saline (PBS), and the mononuclear cells were isolated by Ficoll density-gradient centrifugation. The isolated CLL cells were cultured at $1 \times 10^7$ cells/mL in RPMI 1640 medium containing 10% of fetal bovine serum, 10% autologous plasma, or 50% autologous plasma. Cell death in CLL lymphocytes was evaluated by flow cytometry analysis using annexin V and propidium iodide (PI) double staining. After incubation with increasing concentrations of PatA analogs for 24 hours, CLL cells ($1 \times 10^6$ cells) were stained in 100 μL binding buffer with 5 μL annexin-Cy5, and incubated for 15 minutes in dark at room temperature. After staining, 300 μL binding buffer with 5 μL of 50 μg/mL propidium iodide were added to each tube. Samples were analyzed immediately by flow cytometer. Cells stained positive for either annexin V or PI were considered dead cells. The $IC_{50}$ values of CLL killing were determined by non-linear fitting of the survival curve by the GraphPad Prism software.

TABLE 1

$IC_{50}$ (μM) Values CLL Assay for Representative Pateamine Derivatives.

| Compound | 10% FBS | 10% plasma | 50% plasma |
|---|---|---|---|
| PatA | 0.15 | 0.16 | 0.47 |
| DMDA Pat A | 0.71 | 5.37 | >10 |
| MZ554 | >10 | >10 | — |
| MZ568 | >10 | >10 | — |
| MZ569a | >10 | >10 | — |

TABLE 1-continued

IC$_{50}$ (μM) Values CLL Assay for Representative Pateamine Derivatives.

| Compound | 10% FBS | 10% plasma | 50% plasma |
| --- | --- | --- | --- |
| MZ569b | >10 | >10 | — |
| MZ576 | 3.2 | 6.69 | — |
| MZ578 | 0.83 | 2.01 | 8.12 |
| MZ579 | 0.55 | 1.79 | 7.18 |
| MZ577 | 3.01 | 6.36 | — |
| MZ623 | 0.31 | 0.46 | — |
| MZ624 | 0.37 | 0.65 | — |
| MZ756 | 1.89 | 5.61 | — |
| MZ757 | <0.05 | 0.45 | — |

FIGS. 2A-2D compare IC$_{50}$ dose response curves (% survival of chronic lymphocytic leukemia (CLL) cells as a function of agent concentration (μM)) for pateamine A (PatA) (2A), desmethyl desamino pateamine A (DM-DAPatA) (2B), α-amino pateamine A derivative (MZ578) (2C), and α-amino pateamine A derivative (MZ579) (2D) in 10% fetal bovine serum (FBS), 10% human plasma, and 50% human plasma.

The following examples are provided for the purpose of illustrating, not limiting the invention.

EXAMPLES

General Methods

All reactions were carried out under nitrogen atmosphere in flame-dried glassware. Acetonitrile, dichloromethane, methanol, and tetrahydrofuran were purified by passage through activated molecular sieves or alumina (solvent system). Dimethylformamide (DMF) was purchased and dried over 4 Å molecular sieves. All commercial reagents were used as received. $^1$H NMR spectra were recorded on INOVA-500 or on Brucker-600. $^1$H NMR chemical shifts are reported as δ values in ppm relative to CDCl$_3$ (7.26 ppm), coupling constants (J) are reported in Hertz (Hz), and multiplicity follows convention. Flash column chromatography was performed using 60 Å Silica Gel as a stationary phase using a gradient solvent system (EtOAc/hexanes as eluent unless specified otherwise). MPLC was performed using CombiFlash® Rf 200i (EtOAc/hexanes as eluent). Purification by prep-HPLC was performed on the Agilent 1260 Infinity Preparative-Scale Purification System using a Gemini HPLC column (C18, 5 micron, 100×21.20 mm). Mass spectra were obtained at the center for Chemical Characterization and Analysis (Texas A&M University). Thin layer chromatography (TLC) was performed using glass-backed silica gel 60F$_{254}$.

Example 1

The Preparation of a Representative Pateamine A Amide Derivative

In this example, the preparation of a representative pateamine A amide derivative of the invention, N-((1$^2$Z,3S,6Z,8E,11S,14S)-3-((1E,3E,5E)-7-(dimethylamino)-2,5-dimethylhepta-1,3,5-trien-1-yl)-9,11-dimethyl-5,13-dioxo-4,12-dioxa-1(2,4)-thiazolacycloheptadecaphane-6,8-dien-14-yl)-2,2,2-trifluoroacetamide (MZ579), is described. The preparation is illustrated schematically in FIG. 1.

(S)-4-Isopropylthiazolidine-2-thione (MZ465)

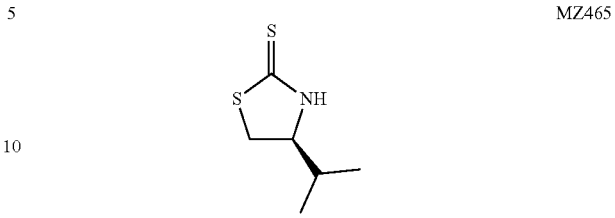

The following procedure gives a higher yield than that reported in the literature. Erik Gálvez, P. R., Felix Urp. (2009) Preparation of (S)-4-Isopropyl-N-Propanoyl-1,3-Thiazolidine-2-Thione, Organic Syntheses 86, 70. A sealed tube was charged with a solution of KOH (2.7 g, 48.4 mmol, 5 equiv.) in 8 mL of water, 2 mL of EtOH, CS$_2$ (2.9 mL, 48.4 mmol, 5 equiv.), and (S)-(+)-2-amino-3-methyl-1-butanol (1.0 g, 9.69 mmol, 1 equiv.). The mixture was heated at 80° C. for 15 hours, purged with N$_2$ to remove the excess CS$_2$, and neutralized by adding aqueous HCl solution (1 M). After extraction with EtOAc (3×60 mL) the organic layer was washed with brine (5 mL), dried over MgSO$_4$, and concentrated in vacuo. The residue was purified on a silica gel chromatography to give the desired product as a yellow solid (1.19 g, 76%). The characterization data match with those in the literature.

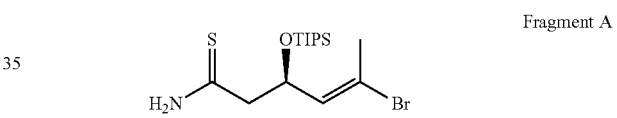

Fragment A

The compound was synthesized from MZ465 using the previously reported procedure. Romo, D., Rzasa, R. M., Shea, H. A., Park, K., Langenhan, J. M., Sun, L., Akhiezer, A., and Liu, J. O. (1998) Total Synthesis and Immunosuppressive Activity of (−)-Pateamine A and Related Compounds: Implementation of a β-Lactam-Based Macrocyclization, J. Am. Chem. Soc. 120, 12237-12254; Low, W. K., Li, J., Zhu, M., Kommaraju, S. S., Shah-Mittal, J., Hull, K., Liu, J. O., and Romo, D. (2014) Second-generation derivatives of the eukaryotic translation initiation inhibitor pateamine A targeting eIF4 Å as potential anticancer agents, Bioorg. Med. Chem. 22, 116-125.

2,2,2-Trichloroethyl-(S)-2-(tert-butoxycarbonylamino)pent-4-enoate (MZ434)

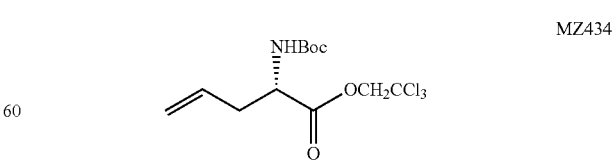

A mixture of (S)-2-(tert-butoxycarbonylamino)pent-4-enoic acid (10.3 g, 47.9 mmol, 1 equiv.), 2,2,2-trichloroethanol (4.62 mL, 47.9 mmol, 1 equiv.), DMAP (585 mg, 4.79 mmol, 0.1 equiv.), and DCC (10.9 mmol, 52.7 mmol, 1.1 equiv.) in 200 mL of THF was stirred at 20° C. under N₂ for 24 hours. The suspension was filtered by a sintered Buchner glass funnel and the precipitates were washed with 20 mL of methyl tert-butyl ether. After concentration in vacuo the residue was purified on a silica gel chromatography (hexanes:methyl tert-butyl ether=30:1→20:1) to give the product as a colorless oil (13.4 g, 81%). ¹H NMR (500 MHz, CDCl₃) δ 5.81-5.67 (m, 1H), 5.23-5.19 (m, 2H), 5.17-5.16 (m, 1H), 4.99 (d, J=7.3 Hz, 1H), 4.91 (d, J=12.0 Hz, 1H), 4.66 (d, J=12.0 Hz, 1H), 4.54-4.48 (m, 1H), 2.69-2.53 (m, 1H), 1.45 (s, 9H). HRMS (ESI⁺): Calcd. For C₁₂H₁₉C₁₃NO₄ ([M+H]⁺), 346.0380. Found: 346.0371.

2,2,2-Trichloroethyl-(S,E)-2-(tert-butoxycarbonylamino)-6-oxohept-4-enoate (MZ456)

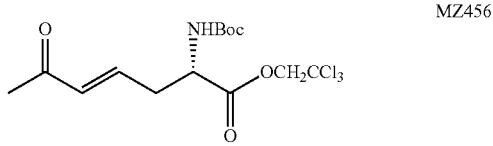

MZ456

An ozone stream was bubbled through the stirred solution of MZ434 (1.54 g, 4.44 mmol, 1 equiv.) in 50 mL of DCM at −78° C. for ca. 10 minutes until the color turned blue. The cold bath was removed and the solution was flushed with N₂ for 30 minutes. Dimethyl sulfide (2.00 mL, 27.0 mmol, 6.1 equiv.) was added and the solution was stirred at 20° C. for 20 hours. After concentration 1-(triphenylphosphoranylidene)-2-propanone (3.54 g, 11.1 mmol, 2.5 equiv.) and 40 mL of THF was added. The mixture was continued to stir at 20° C. for 15 hours followed by concentration. The residue was purified on a silica gel chromatography (hexanes:methyl tert-butyl ether=5:1→3:1) to give the product as a colorless oil (0.94 g, 57%). ¹H NMR (500 MHz, CDCl₃) δ 6.70 (dt, J=15.9 Hz, J=7.3 Hz, 1H), 6.14 (d, J=15.9 Hz, 1H), 5.13-0.509 (m, 1H), 4.92 (d, J=12.0 Hz, 1H), 4.67 (d, J=12.0 Hz, 1H), 4.65-4.61 (m, 1H), 2.89-2.83 (m, 1H), 2.70-2.64 (m, 1H), 2.24 (s, 3H), 1.43 (s, 9H). HRMS (ESI⁺): Calcd. For C₁₄H₂₁C₁₃NO₅ ([M+H]⁺), 388.0485. Found: 388.0481.

(S)-2,2,2-Trichloroethyl-2-(tert-butoxycarbonylamino)-6-oxoheptanoate (MZ442)

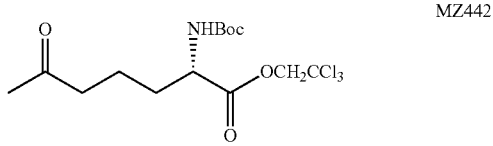

MZ442

A round-bottom flask was charged with MZ456 (6.80 g, 17.5 mmol, 1 equiv.), Pd/C (10 w/w %, 800 mg, 0.752 mmol, 0.043 equiv.), EtOAc (54 mL), and EtOH (6 mL) followed by setting a H₂ balloon on the top of the flask. The mixture was stirred under the H₂ atmosphere at 20° C. for 15 hours and then filtered through a short celite pad. The solution was concentrated and the crude residue was purified on a silica gel chromatography (hexanes:methyl tert-butyl ether=3:1) to provide the product as a colorless oil (5.70 g, 82%). ¹H NMR (500 MHz, CDCl₃) δ 5.07 (d, J=8.3 Hz, 1H), 4.91 (d, J=11.9 Hz, 1H), 4.64 (d, J=11.9 Hz, 1H), 4.43-4.38 (m, 1H), 2.55-2.44 (m, 2H), 2.13 (s, 3H), 1.92-1.84 (m, 1H), 1.74-1.65 (m, 3H), 1.44 (s, 9H). HRMS (ESI⁺): Calcd. For C₁₄H₂₃C₁₃NO₅ ([M+H]⁺), 390.0642. Found: 390.0653.

(S)-2,2,2-Trichloroethyl-7-bromo-2-(tert-butoxycarbonylamino)-6-oxoheptanoate (MZ463)

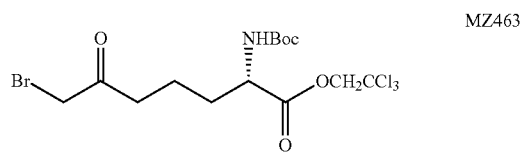

MZ463 n-Butyllithium solution (2.5 M in THF, 12.8 mL, 32.0 mmol, 3 equiv.) was slowly added to a solution of 1,1,1,3,3,3-hexamethyldisilazane (6.79 mL, 32.0 mmol, 3 equiv.) in 200 mL of THF at −78° C. under N₂. The solution was stirred at 0° C. for 20 minutes, cooled to −78° C. and chlorotrimethylsilane (13.6 mL, 106.5 mmol, 10 equiv.) was slowly added followed by MZ442 (3.99 g, 10.65 mmol, 1 equiv.) as a THF solution (20 mL). After 20 minutes anhydrous triethylamine (30 mL, 213 mmol, 20 equiv.) was slowly added. The mixture was continued to stir for 5 minutes and the reaction was quenched with 50 mL of saturated aqueous NaHCO₃ solution and extracted with methyl tert-butyl ether (3×100 mL). The organic layer was washed with brine (5 mL), dried over MgSO₄ and concentrated in vacuo. The residue was dissolved in 10 mL of THF and the solution was added to a stirred suspension of N-bromosuccinimide (1.78 g, 10.0 mmol, 0.94 equiv.) and NaHCO₃ (1.01 g, 12.0 mmol, 1.1 equiv.) in THF (150 mL) at −78° C. under N₂. After stirring for 1.5 hour, the reaction was quenched by adding 30 mL of saturated aqueous NaHCO₃ solution and the mixture was extracted with methyl tert-butyl ether (3×50 mL). The organic layer was washed with brine (5 mL), dried over MgSO₄ and concentrated. The crude residue was purified on a silica gel chromatography (hexanes:methyl tert-butyl ether=10:1→7:1) to provide the product as a yellow oil (3.29 g, 68%). ¹H NMR (500 MHz, CDCl₃) δ 5.05 (d, J=8.3 Hz, 1H), 4.92 (d, J=12.0 Hz, 1H), 4.65 (d, J=12.0 Hz, 1H), 4.45-4.41 (m, 1H), 3.87 (s, 2H), 2.75-2.71 (m, 2H), 1.95-1.89 (m, 1H), 1.80-1.70 (m, 3H), 1.45 (s, 9H). HRMS (ESI⁺): Calcd. For C₁₄H₂₂BrCl₃NO₅ ([M+H]⁺), 467.9747. Found: 467.9772.

2,2,2-Trichloroethyl-(S)-5-(2-((R,E)-4-bromo-2-((triisopropylsilyl)oxy)pent-3-en-1-yl)thiazol-4-yl)-2-((tert-butoxycarbonyl)amino)pentanoate (MZ526b)

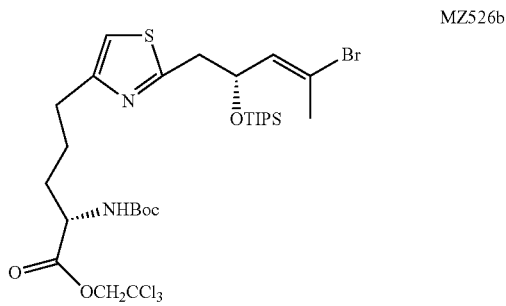

MZ526b

Following the same procedure as in the literature, (Romo, D., Rzasa, R. M., Shea, H. A., Park, K., Langenhan, J. M., Sun, L., Akhiezer, A., and Liu, J. O. (1998) Total Synthesis and Immunosuppressive Activity of (−)-Pateamine A and Related Compounds: Implementation of a β-Lactam-Based Macrocyclization, J. Am. Chem. Soc. 120, 12237-12254) the reaction between MZ463 (2.26 g, 4.81 mmol, 1.3 equiv.) and Fragment A (1.41 g, 3.70 mmol, 1 equiv.) formed the product as a colorless oil (2.08 g, 75%). $^1$H NMR (500 MHz, CDCl$_3$) δ 6.77 (s, 1H), 5.89-5.84 (m, 1H), 5.10 (d, J=8.3 Hz, 1H), 4.92 (d, J=12 Hz, 1H), 4.77 (dt, J=8.8 Hz, J=6.1 Hz, 1H), 4.62 (d, J=12 Hz, 1H), 4.48-4.42 (m, 1H), 3.24 (dd, J=14.3 Hz, J=6.4 Hz, 1H), 3.11 (dd, J=14.3 Hz, J=6.2 Hz, 1H), 2.84-2.69 (m, 2H), 2.10 (s, 3H), 2.02-1.90 (m, 1H), 1.88-1.68 (m, 2H), 1.67-1.60 (m, 1H), 1.44 (s, 9H), 1.02 (s, 21H). HRMS (ESI$^+$): Calcd. For C$_{29}$H$_{49}$BrCl$_3$N$_2$O$_5$SSi ([M+H]$^+$), 749.1380. Found: 749.1349.

2,2,2-Trichloroethyl-(S)-5-(2-((R,E)-4-bromo-2-hydroxypent-3-en-1-yl)thiazol-4-yl)-2-(tert-butoxycarbonylamino)pentanoate (MZ527)

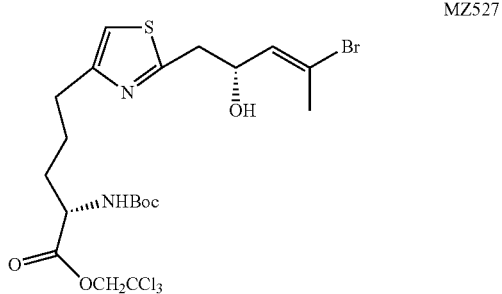

MZ527

To a solution of MZ526b (2.29 g, 3.05 mmol, 1.0 equiv.) in 150 mL of THF at −20° C. under N$_2$ was added a pre-mixed solution of tetrabutylammonium fluoride (1 M in THF, 9.16 mL, 9.16 mmol, 3 equiv.) and acetic acid (423 μL, 7.33 mmol, 2.4 equiv.) under N$_2$. The mixture was kept in a −20° C. freezer for 15 hours, diluted with 200 mL of methyl tert-butyl ether, washed with saturated aqueous NaHCO$_3$ solution (5 mL), water (5 mL) and brine (5 mL). The organic layer was dried over MgSO$_4$ and concentrated in vacuo. The crude residue was purified by MPLC (hexanes:EtOAc=1:1) to give the product as a colorless oil (1.55 g, 85%). $^1$H NMR (500 MHz, CDCl$_3$) δ 6.80 (s, 1H), 5.95 (d, J=8.7 Hz, 1H), 5.10 (d, J=8.1 Hz, 1H), 4.92 (d, J=12.0 Hz, 1H), 4.75-4.71 (m, 1H), 4.63 (d, J=12.0 Hz, 1H), 4.46-4.42 (m, 1H), 3.13 (d, J=5.8 Hz, 2H), 2.82 (dd, J=14.9 Hz, J=7.7 Hz, 1H), 2.76 (dd, J=14.9 Hz, J=7.6 Hz, 1H), 2.29 (s, 3H), 1.98-1.91 (m, 1H), 1.86-1.80 (m, 2H), 1.77-1.70 (m, 1H), 1.44 (s, 9H). OH not observed. HRMS (ESI$^+$): Calcd. For C$_{20}$H$_{29}$BrCl$_3$N$_2$O$_5$S ([M+H]$^+$), 593.0046. Found: 593.0064.

(S)-Triisopropyl(pent-4-yn-2-yloxy)silane (OR-IV-19)

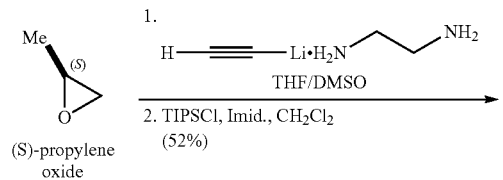

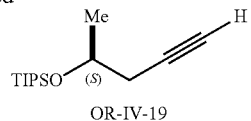

OR-IV-19

(S)-propylene oxide (5 g, 86.09 mmol, 1 equiv.) was dissolved in anhydrous THF (43 mL) and then cooled to 4° C. A solution of lithium acetylide-ethylene diamine complex (9.51 g, 103.31 mmol, 1.2 equiv.) in DMSO (103 mL) was then added dropwise. The reaction mixture was stirred at 22° C. for 36 h and then poured into ice water (150 mL). The mixture was extracted with diethyl ether (4×150 mL), the combined organic fractions were washed with a saturated aqueous solution of ammonium chloride (2×150 mL), dried over sodium sulfate and concentrated under reduced pressure. The residue was dissolved in dichloromethane (100 mL), imidazole (6.45 g, 94.68 mmol, 1.1 equiv.) was added, followed by triisopropylsilyl chloride (18.25 g, 94.68 mmol, 1.1 equiv.). The reaction mixture was stirred at 22° C. for 12 h and then quenched by the addition of a saturated aqueous solution of sodium bicarbonate (100 mL). The organic fraction was washed with water (100 mL), dried over sodium sulfate and concentrated under reduced pressure. The residue was purified by MPLC on silica gel using a gradient of hexanes and ethyl acetate (9:1→1:1) to give the desired product as a colorless oil (10.83 g, 52%). $^1$H NMR (500 MHz, CDCl$_3$) δ 4.10-4.04 (m, 1H), 2.43 (ddd, J=16.5, 3.5, 2.5 Hz, 1H), 2.27 (ddd, J=16.5, 8.0, 2.5 Hz, 1H), 1.98 (t, J=2.5 Hz, 1H), 1.30 (d, J=6.0 Hz, 3H), 1.07-1.04 (m, 21H). LRMS (APCI$^+$): Calcd. For C$_{14}$H$_{28}$OSi ([M]$^+$), 240.19. Found: 240.84.

Ethyl (S,E)-5-methyl-7-((triisopropylsilyl)oxy)oct-4-en-2-ynoate (OR-IV-23)

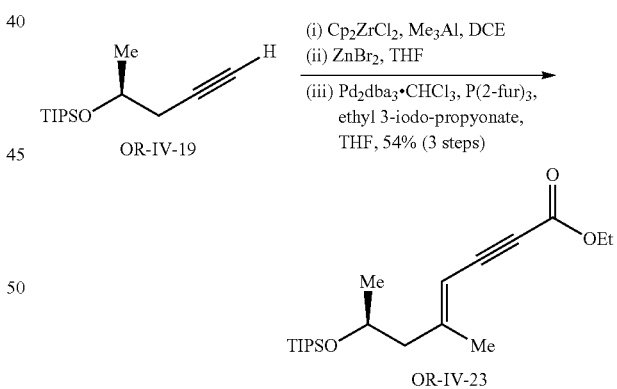

Bis(cyclopentadienyl)-zirconium dichloride (12.16 g, 41.59 mmol, 1 equiv.) was suspended in dichloroethane (100 mL) and then cooled to 0° C. A solution of trimethylaluminum (41.59 mL, 83.17 mmol, 2.0 M in toluene, 2 equiv.) was added, followed by (S)-triisopropyl(pent-4-yn-2-yloxy)silane (OR-IV-19, 10 g, 41.59 mmol, 1 equiv.) dissolved in dichloroethane (20 mL). The reaction mixture was stirred at 22° C. for 12 h, the dichloroethane and excess trimethylaluminum were then removed by evaporation under reduced pressure at 40° C. and anhydrous THF (50 mL) was added. Separately, zinc bromide (10.30 g, 45.75 mmol, 1.1 equiv.) was flame dried and dissolved in anhydrous THF (45.75 mL). The zinc bromide solution was cannulated into the organoaluminum mixture at 0° C. and then the reaction mixture was stirred at 22° C. for 30 minutes. In another flask, tris(dibenzylideneacetone)-dipalladium(0)-chloroform adduct (1.08 g, 1.04 mmol, 0.025 equiv.) was dissolved in anhydrous THF (50 mL) and then tri(2-furyl)phosphine (1.45 g, 6.24 mmol, 0.15 equiv.) was added at 0° C. and stirred for 10 min. Ethyl 3-iodopropynoate (10.25 g, 45.75 mmol, 1.1 equiv.) was added and the resulting solution was added via cannula to the flask containing the organozinc solution. The reaction flask was protected from light and stirred at 22° C. for 16 h. The reaction was quenched with water (150 mL) and then diluted with ether (100 mL). The aqueous phase was extracted with ether (2×200 mL), the organic fractions were combined, washed with brine (200 mL), dried over sodium sulfate, filtered and concentrated under reduced pressure. The residue was purified by MPLC on silica gel using a gradient of hexanes and ethyl acetate (9:1→1:1) to give the desired product as a light yellow oil (7.94 g, 54%). $^1$H NMR (500 MHz, CDCl$_3$) δ 5.41 (s, 1H), 4.25 (q, J=7.0 Hz, 2H), 4.15-4.09 (m, 1H), 2.41 (dd, J=13.0, 5.5 Hz, 1H), 2.25 (dd, J=13.5, 7.0 Hz, 1H), 2.01 (s, 3H), 1.32 (t, J=7.0 Hz, 3H), 1.14 (d, J=6.0 Hz, 3H), 1.07-1.05 (m, 21H). LRMS (APCI$^+$): Calcd. For C$_{20}$H$_{36}$O$_3$Si ([M]$^+$), 352.24. Found: 352.33.

(S,E)-5-methyl-7-((triisopropylsilyl)oxy)oct-4-en-2-ynoic acid (Fragment F)

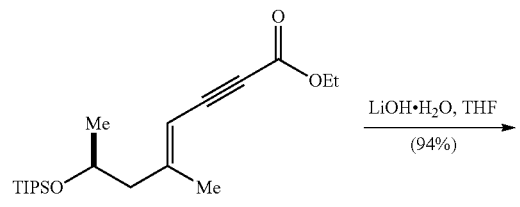

Ethyl (S,E)-5-methyl-7-((triisopropylsilyl)oxy)oct-4-en-2-ynoate (OR-IV-23, 5.0 g, 14.18 mmol, 1 equiv.) was dissolved in THF/H$_2$O (1:1 v/v, 100 mL) and then lithium hydroxide monohydrate (1.19 g, 28.36 mmol, 2 equiv.) was added. The reaction mixture was stirred at 22° C. for 8 h and then quenched by the addition of a hydrochloric acid solution (50 mL, 2 M). The mixture was extracted with ethyl acetate (3×50 mL), the organic fractions were combined, dried over sodium sulfate, filtered and concentrated under reduced pressure. The residue was purified by MPLC on silica gel using a gradient of hexanes and ethyl acetate (4:1→1:9) to give the desired product as a light yellow oil (4.325 g, 94%). $^1$H NMR (500 MHz, CDCl$_3$) δ 10.05 (bs, 1H) 5.44 (q, J=1.0 Hz, 1H), 4.17-4.11 (m, 1H), 2.42 (dd, J=14.0, 6.0 Hz, 1H), 2.27 (dd, J=14.0, 7.0 Hz, 1H), 2.03 (d, J=1.0 Hz, 3H), 1.15 (d, J=6.0 Hz, 3H), 1.07-1.05 (m, 21H). HRMS (ESI): Calcd. For C$_{18}$H$_{31}$O$_3$Si ([M–H]$^+$), 323.2047. Found: 323.2061.

(S,E)-4-Bromo-1-(4-((S)-4-(tert-butoxycarbonyl amino)-5-oxo-5-(2,2,2-trichloroethoxy)pentyl)-3λ$^4$-thiazol-2-yl)pent-3-en-2-yl (S,E)-5-methyl-7-(triisopropylsilyloxy)oct-4-en-2-ynoate (MZ530)

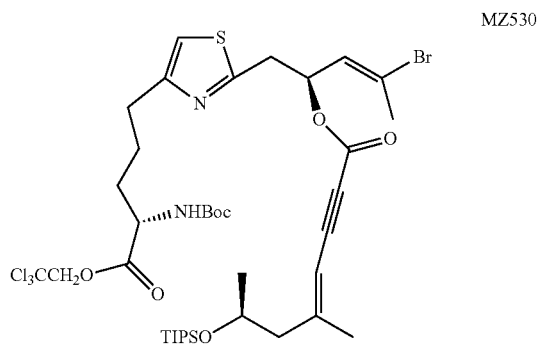

Following the same procedure as in the literature (Romo, D., Choi, N. S., Li, S., Buchler, I., Shi, Z., and Liu, J. O. (2004) Evidence for Separate Binding and Scaffolding Domains in the Immunosuppressive and Antitumor Marine Natural Product, Pateamine A: Design, Synthesis, and Activity Studies Leading to a Potent Simplified Derivative, *J. Am. Chem. Soc.* 126, 10582-10588), MZ527 (950 mg, 1.60 mmol, 1 equiv.) was reacted with Fragment F (623 mg, 1.92 mmol, 1.2 equiv.) to afford the product as a colorless oil (1.20 g, 83%). $^1$H NMR (500 MHz, CDCl$_3$) δ 6.80 (s, 1H), 5.89-5.86 (m, 1H), 5.73 (dt, J=9.6 Hz, J=6.7 Hz, 1H), 5.40 (s, 1H), 5.12 (d, J=8.1 Hz, 1H), 4.92 (d, J=12.0 Hz, 1H), 4.63 (d, J=12.0 Hz, 1H), 4.46-4.42 (m, 1H), 4.15-4.09 (m, 1H), 3.38 (dd, J=14.8 Hz, J=7.1 Hz, 1H), 3.27 (dd, J=14.8 Hz, J=6.4 Hz, 1H), 2.83-2.72 (m, 2H), 2.41 (dd, J=13.3 Hz, J=5.4 Hz, 1H), 2.28 (d, J=1.1 Hz, 3H), 2.25 (dd, J=13.3 Hz, J=6.9 Hz, 1H), 2.01 (s, 3H), 1.98-1.91 (m, 1H), 1.87-1.80 (m, 2H), 1.78-1.71 (m, 1H), 1.44 (s, 9H), 1.13 (d, J=6.0 Hz, 3H), 1.05 (s, 21H). HRMS (ESI$^+$): Calcd. For C$_{38}$H$_{59}$BrCl$_3$N$_2$O$_7$SSi ([M+H]$^+$), 901.2041. Found: 901.2099.

(S,E)-4-Bromo-1-(4-((S)-4-(tert-butoxycarbonylamino)-5-oxo-5-(2,2,2-trichloroethoxy)pentyl)thiazol-2-yl)pent-3-en-2-yl (S,E)-7-hydroxy-5-methyloct-4-en-2-ynoate (MZ533)

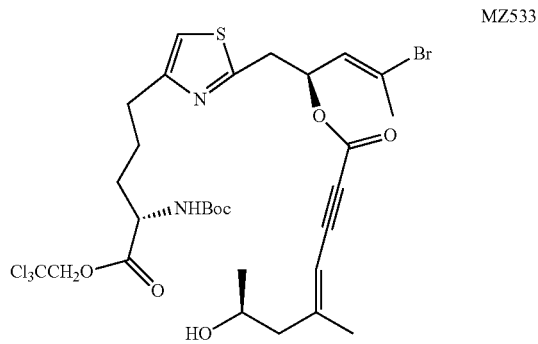

Tetrabutylammonium fluoride (1 M in THF, 5 mL, 5.0 mmol) was mixed with HF/py (70 w/w % HF, 138 μL, 5.3 mmol) at 0° C. and 1.69 mL of the mixture was added to a solution of MZ530 (290 mg, 0.322 mmol) in THF (1.2 mL) at 0° C. The reaction was maintained at the same temperature for 6 hours. The mixture was diluted with 100 mL of DCM and was washed with saturated aqueous NaHCO$_3$ solution (5 mL), water (5 mL), and brine (5 mL). The organic layer was dried over MgSO$_4$ and concentrated. The crude residue was purified on a silica gel chromatography to give the desired product as a colorless oil (185 mg, 77%). $^1$H NMR (500 MHz, CDCl$_3$) δ 6.81 (s, 1H), 5.89-5.86 (m, 1H), 5.78 (dt, J=9.4 Hz, J=6.6 Hz, 1H), 5.47-5.46 (m, 1H), 5.14 (d, J=8.3 Hz, 1H), 4.92 (d, J=12.0 Hz, 1H), 4.63 (d, J=12.0 Hz, 1H), 4.45-4.41 (m, 1H), 4.03-3.97 (m, 1H), 3.38 (dd, J=14.8 Hz, J=7.3 Hz, 1H), 3.27 (dd, J=14.8 Hz, J=6.2 Hz, 1H), 2.83-2.73 (m, 2H), 2.33-2.25 (m, 2H), 2.29 (d, J=1.2 Hz, 3H), 2.03 (d, J=1.1 Hz, 3H), 1.97-1.89 (m, 1H), 1.86-1.80 (m, 2H), 1.78-1.71 (m, 1H), 1.44 (s, 9H), 1.22 (d, J=6.2 Hz, 3H). OH not observed. HRMS (ESI$^+$): Calcd. For C$_{29}$H$_{39}$BrCl$_3$N$_2$O$_7$S ([M+H]$^+$), 743.0727. Found: 743.0755.

(S)-5-(2-(((S,E)-4-Bromo-2-(((S,E)-7-hydroxy-5-methyloct-4-en-2-ynoyl)oxy)pent-3-en-1-yl) thiazol-4-yl)-2-(tert-butoxycarbonylamino)pentanoic acid (MZ536)

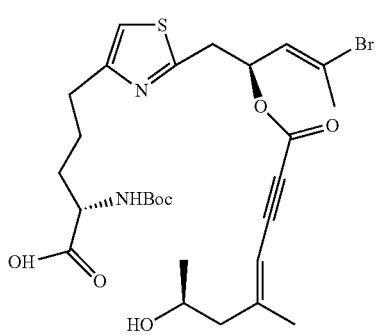

MZ536

Following the known procedure, (Romo, D., Rzasa, R. M., Shea, H. A., Park, K., Langenhan, J. M., Sun, L., Akhiezer, A., and Liu, J. O. (1998) Total Synthesis and Immunosuppressive Activity of (−)-Pateamine A and Related Compounds: Implementation of a β-Lactam-Based Macrocyclization, J. Am. Chem. Soc. 120, 12237-12254) MZ536 was synthesized from MZ533 (400 mg, 0.537 mmol) as a colorless oil (241 mg, 73%). $^1$H NMR (500 MHz, CDCl$_3$) δ 6.86 (s, 1H), 5.88-5.86 (m, 1H), 5.77-5.72 (m, 1H), 5.46 (s, 1H), 5.29 (d, J=7.8 Hz, 1H), 4.35-4.31 (m, 1H), 4.05-3.99 (m, 1H), 3.44 (dd, J=14.8 Hz, J=7.6 Hz, 1H), 3.35 (dd, J=14.8 Hz, J=5.7 Hz, 1H), 2.79 (t, J=6.9 Hz, 2H), 2.33-2.25 (m, 2H), 2.29 (s, 3H), 2.01 (s, 3H), 1.93-1.86 (m, 1H), 1.81-1.74 (m, 3H), 1.44 (s, 9H), 1.22 (d, J=6.2 Hz, 3H). OH not observed. HRMS (ESI$^+$): Calcd. For C$_{27}$H$_{38}$BrN$_2$O$_7$S ([M+H]$^+$), 613.1583. Found: 613.1568.

tert-Butyl ((1$^2$Z,3S,8E,11S,14S)-3-((E)-2-bromoprop-1-en-1-yl)-9,11-dimethyl-5,13-dioxo-4, 12-dioxa-1 (2,4)-thiazolacycloheptadecaphane-6-yn-8-en-14-yl)carbamate (MZ538)

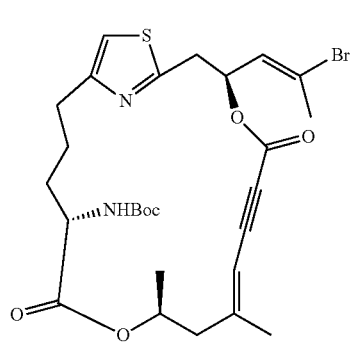

MZ538

Following the known procedure, (Romo, D., Choi, N. S., Li, S., Buchler, I., Shi, Z., and Liu, J. O. (2004) Evidence for Separate Binding and Scaffolding Domains in the Immunosuppressive and Antitumor Marine Natural Product, Pateamine A: Design, Synthesis, and Activity Studies Leading to a Potent Simplified Derivative, J. Am. Chem. Soc. 126, 10582-10588.) MZ536 (52 mg, 0.085 mmol) afforded the desired product as a colorless oil (31 mg, 68%). $^1$H NMR (500 MHz, CDCl$_3$) δ 6.79 (s, 1H), 6.03 (d, J=9.1 Hz, 1H), 5.93-5.87 (m, 1H), 5.40 (s, 1H), 5.27-5.21 (m, 1H), 5.14 (d, J=7.7 Hz, 1H), 4.31-4.27 (m, 1H), 3.35-3.27 (m, 2H), 2.79 (t, J=7.3 Hz, 2H), 2.43-2.30 (m, 2H), 2.41 (s, 3H), 1.93 (s, 3H), 1.90-1.86 (m, 1H), 1.77-1.69 (m, 1H), 1.67-1.60 (m, 2H), 1.45 (s, 9H), 1.29 (d, J=6.2 Hz, 3H). HRMS (ESI$^+$): Calcd. For C$_{27}$H$_{36}$BrN$_2$O$_6$S ([M+H]$^+$), 595.1477. Found: 595.1474.

tert-Butyl-((1$^2$Z,3S,6Z,8E,11S,14S)-3-((E)-2-bromoprop-1-en-1-yl)-9,11-dimethyl-5,13-dioxo-4,12-dioxa-1(2,4)-thiazolacycloheptadecaphane-6,8-dien-14-yl)carbamate (MZ554)

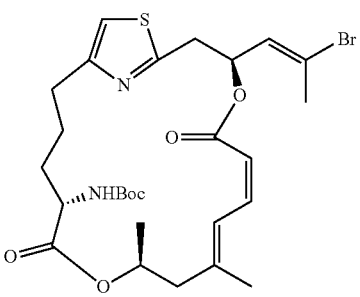

MZ554

A H$_2$ balloon was placed on the top of a flask containing MZ538 (53 mg, 0.089 mmol, 1 equiv.), lindlar catalyst (25 mg), and MeOH (10 mL). The mixture was stirred at 20° C. for 2.5 hours until no starting material visible on TLC and was filtered through a cotton pad which was rinsed with 5 mL of EtOAc. The solvents were evaporated in vacuo and the crude residue was purified on a silica gel chromatography to provide the product as a colorless oil (50 mg, 94%).

¹H NMR (500 MHz, CDCl₃) δ 6.94 (d, J=12.0 Hz, 1H), 6.78 (s, 1H), 6.69 (t, J=11.6 Hz, 1H), 6.06 (td, J=9.7 Hz, J=4.1 Hz, 1H), 6.00-5.98 (m, 1H), 5.45 (d, J=11.5 Hz, 1H), 5.29-5.23 (m, 1H), 4.93 (d, J=8.9 Hz, 1H), 4.21-4.16 (m, 1H), 3.25-3.15 (m, 2H), 2.86-2.81 (m, 1H), 2.71-2.65 (m, 1H), 2.43 (d, J=1.1 Hz, 3H), 2.40 (dd, J=13.5 Hz, J=11.2 Hz, 1H), 2.23 (d, J=13.5 Hz, 1H), 1.94-1.82 (m, 3H), 1.81 (s, 3H), 1.73-1.66 (m, 1H), 1.45 (s, 9H), 1.29 (d, J=6.3 Hz, 3H). HRMS (ESI⁺): Calcd. For $C_{27}H_{38}BrN_2O_6S$ ([M+H]⁺), 597.1634. Found: 597.1653.

(1²Z,3S,6Z,8E,11S,14S)-14-Amino-3-((E)-2-bromoprop-1-en-1-yl)-9,11-dimethyl-4,12-dioxa-1(2,4)-thiazolacycloheptadecaphane-6,8-diene-5,13-dione (MZ556)

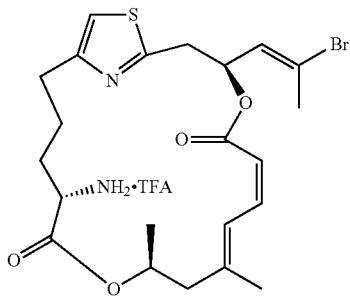

MZ556

A solution of trifluoroacetic acid (0.4 mL) in DCM (1.6 mL) was cooled to 0° C. and added to MZ554 (36 mg, 0.060 mmol) at 0° C. under N₂. The reaction was kept in a 4° C. refrigerator for 15 hours, and the solvents were evaporated while the flask was kept at 0° C. The crude residue was purified on a silica gel chromatography (dichloromethane:MeOH=20:1) to give the product as a colorless oil in the form of a TFA salt (35 mg, 98%). ¹H NMR (500 MHz, CDCl₃) δ 6.94 (d, J=10.9 Hz, 1H), 6.87 (s, 1H), 6.73 (t, J=11.3 Hz, 1H), 6.00 (brs, 2H), 5.51 (d, J=11.3 Hz, 1H), 5.35 (brs, 1H), 3.85 (brs, 1H), 3.21 (brs, 2H), 2.80 (brs, 1H), 2.68 (brs, 1H), 2.46 (d, J=12.6 Hz, 1H), 2.39 (s, 3H), 2.28 (d, J=12.6 Hz, 1H), 1.91-1.81 (m, 3H), 1.77 (s, 3H), 1.73-1.64 (m, 1H), 1.28 (d, J=4.7 Hz, 3H). NH₂ not observed. HRMS (ESI⁺): Calcd. For $C_{22}H_{30}BrN_2O_4S$ ([M+H]⁺), 497.1110. Found: 497.1117.

1,1,1-Trichloro-2-methylpropan-2-yl ((1²Z,3S,6Z,8E,11S,14S)-3-((E)-2-bromoprop-1-en-1-yl)-9,11-dimethyl-5,13-dioxo-4,12-dioxa-1(2,4)-thiazolacycloheptadecaphane-6,8-dien-1⁴-yl) carbamate (MZ569a)

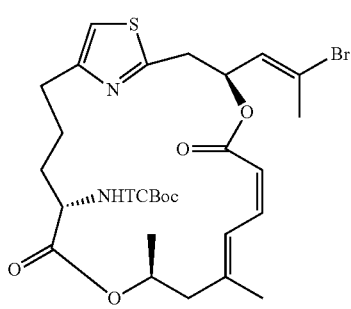

MZ569a

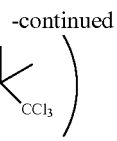

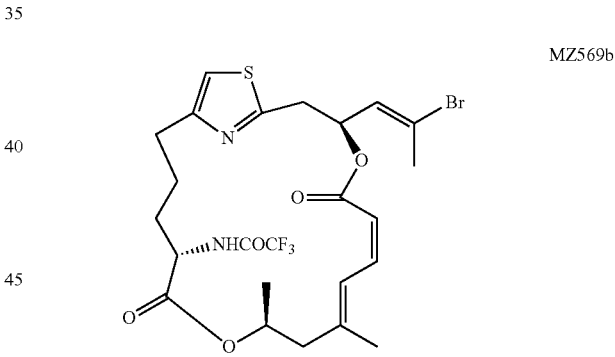

Following the known procedure, (Romo, D., Rzasa, R. M., Shea, H. A., Park, K., Langenhan, J. M., Sun, L., Akhiezer, A., and Liu, J. O. (1998) Total Synthesis and Immunosuppressive Activity of (−)-Pateamine A and Related Compounds: Implementation of a β-Lactam-Based Macrocyclization, J. Am. Chem. Soc. 120, 12237-12254) MZ556 (4.5 mg, 0.0074 mmol) afforded the desired product as a colorless oil (3.7 mg, 71%). ¹H NMR (500 MHz, CDCl₃) δ 6.95 (d, J=11.8 Hz, 1H), 6.78 (s, 1H), 6.70 (t, J=11.6 Hz, 1H), 6.07 (td, J=9.4 Hz, J=4.6 Hz, 1H), 6.00-5.97 (m, 1H), 5.45 (d, J=11.5 Hz, 1H), 5.29 (d, J=8.6 Hz, 1H), 5.28-5.23 (m, 1H), 4.18 (ddd, J=9.7 Hz, J=9.3 Hz, J=4.4 Hz, 1H), 3.21-3.17 (m, 2H), 2.88-2.82 (m, 1H), 2.69 (ddd, J=14.9 Hz, J=9.0 Hz, J=5.1 Hz, 1H), 2.42 (s, 3H), 2.40 (dd, J=13.6 Hz, J=11.1 Hz, 1H), 2.23 (d, J=13.6 Hz, 1H), 1.93 (s, 3H), 1.90 (s, 3H), 1.82 (s, 3H), 1.76-1.69 (m, 2H), 1.63-1.58 (m, 1H), 1.51-1.45 (m, 1H), 1.29 (d, J=6.3 Hz, 3H). HRMS (ESI⁺): Calcd. For $C_{27}H_{35}BrCl_3N_2O_6S$ ([M+H]⁺), 699.0465. Found: 699.0427.

N-((1²Z,3S,6Z,8E,11S,14S)-3-((E)-2-Bromoprop-1-en-1-yl)-9,11-dimethyl-5,13-dioxo-4,12-dioxa-1(2,4)-thiazolacycloheptadecaphane-6,8-dien-1⁴-yl)-2,2,2-trifluoroacetamide (MZ569b)

MZ569b

To the solution of MZ556 (9.2 mg, 0.015 mmol, 1 equiv.) in 0.6 mL of DCM was added pyridine (0.3 mL, in excess) at 0° C. followed by trifluoroacetic anhydride (10.5 mL, 0.075 mmol, 5 equiv.). After 30 minutes the mixture was warmed to 20° C. and continued to stir for 2 hours before being concentrated. The residue was purified on a silica gel chromatography (hexanes:EtOAc=5:1) to give the product as a colorless oil (6.8 mg, 76%). ¹H NMR (500 MHz, CDCl₃) δ 6.98 (d, J=11.7 Hz, 1H), 6.94 (d, J=8.1 Hz, 1H), 6.78 (s, 1H), 6.73 (t, J=11.6 Hz, 1H), 6.06 (td, J=9.2 Hz, J=4.2 Hz, 1H), 6.02-5.90 (m, 1H), 5.51 (d, J=11.3 Hz, 1H), 5.29-5.23 (m, 1H), 4.41-4.36 (m, 1H), 3.26-3.19 (m, 2H), 2.88-2.82 (m, 1H), 2.67-2.62 (m, 1H), 2.43 (dd, J=13.7 Hz, J=11.4 Hz, 1H), 2.42 (s, 3H), 2.23 (d, J=13.7 Hz, 1H), 1.89-1.79 (m, 3H), 1.83 (s, 3H), 1.52-1.47 (m, 1H), 1.31 (d, J=6.3 Hz, 3H). HRMS (ESI⁺): Calcd. For $C_{24}H_{29}BrF_3N_2O_5S$ ([M+H]⁺), 593.0933. Found: 593.0951.

1,1,1-Trichloro-2-methylpropan-2-yl((1²Z,3S,6Z,8E, 11S,14S)-3-((1E,3E,5E)-7-(dimethylamino)-2,5-dimethylhepta-1,3,5-trien-1-yl)-9,11-dimethyl-5,13-dioxo-4,12-dioxa-1 (2,4)-thiazol acycloheptadecaphane-6,8-dien-14-yl)carbamate (MZ576)

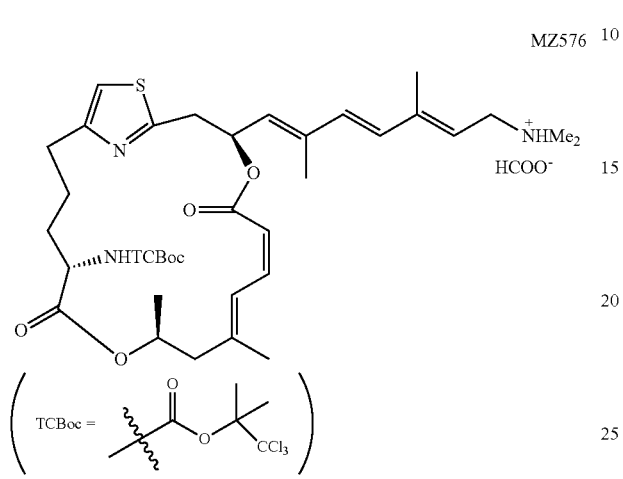

The coupling between MZ569a (7.0 mg, 0.010 mmol, 1 equiv.) and Fragment G (8.3 mg, 0.020 mmol, 2 equiv.) followed the known procedure. Low, W. K., Li, J., Zhu, M., Kommaraju, S. S., Shah-Mittal, J., Hull, K., Liu, J. O., and Romo, D. (2014) Second-generation derivatives of the eukaryotic translation initiation inhibitor pateamine A targeting eIF4 Å as potential anticancer agents, Bioorg. Med. Chem. 22, 116-125. The reaction mixture was kept at 20° C. for 15 hours and transferred directly to a silica gel chromatography for purification (dichloromethane:MeOH:triethylamine=50:1:0.1). The product was further purified by the Prep-HPLC (solvent A: $H_2O$ buffered with 8 mM HCOOH and 12 mM $NH_3,H_2O$, pH=9.0; solvent B: $CH_3CN/H_2O$ (9:1 v/v) buffered with 8 mM HCOOH and 12 mM $NH_3,H_2O$; isocratic elution, solvent A/solvent B=1:4). The collected fractions were concentrated to give a mixture of the product and solid ammonium formate, upon which DCM (10 mL) was added and the suspension was filtered through a sintered Buchner glass funnel. The precipitates were rinsed with extra dichloromethane (2×5 mL). After concentration in vacuo the product was obtained as a colorless oil in the form a salt with formic acid (4.5 mg, 73%). $^1$H NMR (500 MHz, $CDCl_3$) δ 8.49 (brs, 1H), 6.97 (d, J=11.8 Hz, 1H), 6.80 (s, 1H), 6.69 (t, J=11.6 Hz, 1H), 6.38 (d, J=16.0 Hz, 1H), 6.32 (d, J=16.0 Hz, 1H), 6.28 (ddd, J=10.3 Hz, J=9.0 Hz, J=3.5 Hz, 1H), 5.67 (t, J=7.6 Hz, 1H), 5.63 (d, J=8.9 Hz, 1H), 5.48 (d, J=11.4 Hz, 1H), 5.30 (d, J=8.9 Hz, 1H), 5.30-5.25 (m, 1H), 4.19 (ddd, J=9.7 Hz, J=8.9 Hz, J=4.6 Hz, 1H), 3.59 (d, J=7.7 Hz, 2H), 3.24 (dd, J=14.5 Hz, J=10.5 Hz, 1H), 3.19 (dd, J=14.5 Hz, J=3.6 Hz, 1H), 2.89-2.83 (m, 1H), 2.69 (ddd, J=13.5 Hz, J=8.6 Hz, J=5.2 Hz, 1H), 2.60 (s, 6H), 2.42 (dd, J=13.5 Hz, J=11.5 Hz, 1H), 2.24 (d, J=13.5 Hz, 1H), 1.96 (s, 3H), 1.94 (s, 3H), 1.92-1.88 (m, 1H), 1.91 (s, 3H), 1.86 (s, 3H), 1.81 (s, 3H), 1.78-1.73 (m, 1H), 1.30 (d, J=6.3 Hz, 3H), 1.28-1.20 (m, 2H). HRMS (ESI$^+$): Calcd. For $C_{35}H_{49}Cl_3N_3O_6S$ ([M+H]$^+$), 744.2408. Found: 744.2500.

(12Z,3S,6Z,8E,11S,14S)-14-Amino-3-((1E,3E,5E)-7-(dimethylamino)-2,5-dimethylhepta-1,3,5-trien-1-yl)-9,11-dimethyl-4,12-dioxa-1(2,4)-thiazolacycloheptadecaphane-6,8-diene-5,13-dione (MZ577)

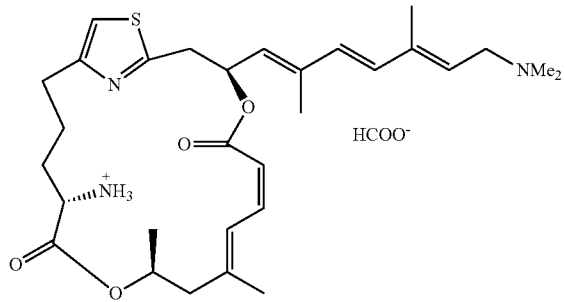

A mixture of MZ576 (1.4 mg, 1.8 μmol), Cd—Pb couple (5.5 mg), aqueous $NH_4OAc$ solution (1 M, 50 μL), $H_2O$ (150 μL), and THF (200 μL) was stirred at 20° C. under $N_2$. After 1 hour an extra portion of Cd—Pb couple (1.4 mg) was added and the mixture was continued to stir for another 30 minutes. The solvents were evaporated and $CHCl_3$ (5 mL) was added to the residue. The suspension was filtered through a sintered Buchner glass funnel and the solvent was concentrated. The crude residue was purified by prep-HPLC following the same procedure as in MZ576 to give the product in the form of a salt with formic acid (0.5 mg, 47%). $^1$H NMR (500 MHz, $CDCl_3$) δ 8.44 (brs, 1H), 6.98 (d, J=11.7 Hz, 1H), 6.77 (s, 1H), 6.69 (t, J=11.6 Hz, 1H), 6.38 (d, J=15.9 Hz, 1H), 6.32 (d, J=16.0 Hz, 1H), 6.27 (td, J=8.9 Hz, J=5.2 Hz, 1H), 5.67 (t, J=7.6 Hz, 1H), 5.63 (d, J=8.8 Hz, 1H), 5.46 (d, J=11.5 Hz, 1H), 5.27-5.21 (m, 1H), 3.55 (d, J=7.7 Hz, 2H), 4.82 (q, J=4.7 Hz, 1H), 3.23-3.19 (m, 2H), 2.88-2.82 (m, 1H), 2.73 (ddd, J=13.9 Hz, J=8.2 Hz, J=5.1 Hz, 1H), 2.57 (s, 6H), 2.42 (dd, J=13.5 Hz, J=11.0 Hz, 1H), 2.22 (d, J=13.5 Hz, 1H), 1.97 (s, 3H), 1.94-1.88 (m, 1H), 1.86 (s, 3H), 1.82 (s, 3H), 1.68-1.61 (m, 1H), 1.28 (d, J=6.3 Hz, 3H), 1.23-1.15 (m, 2H). $NH_2$ not observed. HRMS (ESI): Calcd. For $C_{30}H_{44}N_3O_4S$ ([M+H]$^+$), 542.3053. Found: 542.3097.

N-((1Z,3S,6Z,8E,11S,14S)-3-((1E,3E,5E)-7-(dimethylamino)-2,5-dimethylhepta-1,3,5-trien-1-yl)-9, 11-dimethyl-5,13-dioxo-4,12-dioxa-1(2,4)-thiazolacycloheptadecaphane-6,8-dien-14-yl)-2,2,2-trifluoroacetamide (MZ579)

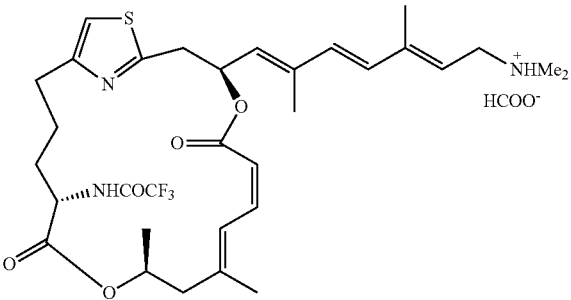

The coupling between MZ569b (6.8 mg, 0.0115 mmol, 1 equiv.) and Fragment G (9.5 mg, 0.023 mmol, 2 equiv.) followed the known procedure. Low, W. K., Li, J., Zhu, M., Kommaraju, S. S., Shah-Mittal, J., Hull, K., Liu, J. O., and Romo, D. (2014) Second-generation derivatives of the eukaryotic translation initiation inhibitor pateamine A targeting eIF4 Å as potential anticancer agents, Bioorg. Med. Chem. 22, 116-125. The purification was the same as for MZ576. The desired product was obtained in the form of salt with formic acid as a colorless oil (5.5 mg, 70%). $^1$H NMR (500 MHz, CDCl$_3$) δ 8.51 (brs, 1H), 7.00 (d, J=11.9, 1H), 6.99 (d, J=8.3 Hz, 1H), 6.80 (s, 1H), 6.71 (t, J=11.6 Hz, 1H), 6.39 (d, J=15.8 Hz, 1H), 6.31 (d, J=15.8 Hz, 1H), 6.25 (ddd, J=10.2 Hz, J=8.9 Hz, J=3.7 Hz, 1H), 5.67 (t, J=7.3 Hz, 1H), 5.64 (d, J=9.1 Hz, 1H), 5.53 (d, J=11.3 Hz, 1H), 5.31-5.24 (m, 1H), 4.41-4.36 (m, 1H), 3.53 (d, J=7.6 Hz, 2H), 3.25 (dd, J=14.5 Hz, J=10.2 Hz, 1H), 3.20 (dd, J=14.5 Hz, J=3.7 Hz, 1H), 2.89-2.83 (m, 1H), 2.69-2.63 (m, 1H), 2.55 (s, 6H), 2.44 (dd, J=13.8 Hz, J=11.3 Hz, 1H), 2.25 (d, J=13.8 Hz, 1H), 1.95 (d, J=1.2 Hz, 3H), 1.91-1.88 (m, 1H), 1.85-1.83 (m, 2H), 1.86 (s, 3H), 1.81 (s, 3H), 1.56-1.48 (m, 1H), 1.31 (d, J=6.2 Hz, 3H). HRMS (ESI$^+$): Calcd. For $C_{32}H_{43}F_3N_3O_5S$ ([M+H]$^+$), 638.2876. Found: 638.2768.

Example 2

The Preparation of a Representative Pateamine A Amide Derivative

In this example, the preparation of a representative pateamine A amide derivative of the invention, N-((1$^2$Z,3S,6Z,8E,11S,14S)-3-((1E,3E,5E)-7-(dimethylamino)-2,5-dimethylhepta-1,3,5-trien-1-yl)-9,11-dimethyl-5,13-dioxo-4,12-dioxa-1(2,4)-thiazolacycloheptadecaphane-6,8-dien-14-yl) acetamide (MZ623), is described.

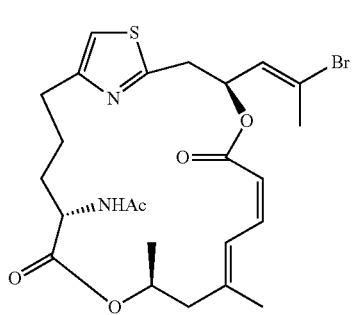

MZ620

N-((1$^2$Z,3S,6Z,8E,11S,14S)-3-((E)-2-bromoprop-1-en-1-yl)-9,11-dimethyl-5,13-dioxo-4,12-dioxa-1 (2,4)-thiazolacycloheptadecaphane-6,8-dien-14-yl) acetamide (MZ620). To a solution of MZ556 (6.5 mg, 0.011 mmol, 1 equiv.) in 0.4 mL of CH$_2$Cl$_2$ were added pyridine (0.2 mL, excess) and AcCl (3.8 μL, 0.053 mmol, 5 equiv.) at 0° C. The temperature was increased to 20° C. within 1 h and the reaction was continued for 15 hours. The mixture was diluted with 25 mL of EtOAc, washed with H$_2$O and brine. The organic phase was dried over MgSO$_4$ and concentrated in vacuo. The residue was purified by a flash chromatography (CH$_2$C12: MTBE=2:1) to give the desired product as a colorless oil (3.4 mg, 60%). $^1$H NMR (500 MHz, CDCl$_3$) δ 6.94 (d, J=11.6 Hz, 1H), 6.80 (s, 1H), 6.71 (t, J=11.6 Hz, 1H), 6.05 (td, J=9.7 Hz, J=3.2 Hz, 1H), 6.01 (app. d, J=9.1 Hz, 1H), 5.89 (d, J=8.7 Hz, 1H), 5.49 (d, J=11.3 Hz, 1H), 5.30-5.24 (m, 1H), 4.53 (td, J=8.9 Hz, J=5.0 Hz, 1H), 3.24 (dd, J=14.4 Hz, J=9.9 Hz, 1H), 3.19 (dd, J 14.4=Hz, J=2.9 Hz, 1H), 2.86-2.80 (m, 1H), 2.68-2.62 (m, 1H), 2.43 (d, J=14.2 Hz, 1H), 2.41 (s, 3H), 2.26 (d, J=14.2 Hz, 1H), 2.04 (s, 3H), 1.85-1.78 (m, 3H), 1.81 (s, 3H), 1.73-1.66 (m, 1H), 1.29 (d, J=6.2 Hz, 3H). HRMS (ESI$^+$): Calcd. For $C_{24}H_{32}BrN_2O_5S$ ([M+H]$^+$), 539.1215. Found: 539.1191.

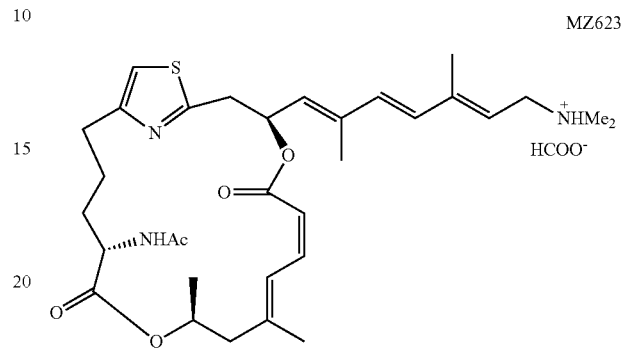

MZ623

N-((1$^2$Z,3S,6Z,8E,11S,14S)-3-((E,3E,5E)-7-(dimethylamino)-2,5-dimethylhepta-1,3,5-trien-1-yl)-9,11-dimethyl-5,13-dioxo-4,12-dioxa-1(2,4)-thiazolacycloheptadecaphane-6,8-dien-14-yl) acetamide (MZ623). The coupling between MZ620 (2.0 mg, 0.0037 mmol, 1 equiv.) and Fragment G (3.1 mg, 0.0074 mmol, 2 equiv.) was based on the known procedure. Low, W. K., Li, J., Zhu, M., Kommaraju, S. S., Shah-Mittal, J., Hull, K., Liu, J. O., and Romo, D. (2014) Second-generation derivatives of the eukaryotic translation initiation inhibitor pateamine A targeting eIF4 Å as potential anticancer agents, Bioorg. Med. Chem. 22, 116-125. The purification procedure was the same as that of MZ576, but the product still contained certain amount of impurities. Further purified on prep-HPLC using a modified condition (solvent A: H$_2$O buffered with 8 mM HCOOH and 12 mM NH$_3$,H$_2$O, pH=9.0; solvent B: methanol; gradient elution, solvent A/solvent B=2:3-1:4 within 12 minutes) gave the pure product in the form of salt with formic acid as a colorless oil (0.65 mg, 30%). $^1$H NMR (500 MHz, CDCl$_3$) δ 8.53 (brs, 1H), 6.96 (d, J=11.9 Hz, 1H), 6.82 (s, 1H), 6.69 (t, J=11.5 Hz, 1H), 6.38 (d, J=15.9 Hz, 1H), 6.28 (d, J=15.9 Hz, 1H), 6.25 (ddd, J=10.8 Hz, J=8.7 Hz, J=3.3 Hz, 1H), 5.91 (d, J=8.6 Hz, 1H), 5.66 (t, J=7.2 Hz, 1H), 5.62 (d, J=8.7 Hz, 1H), 5.52 (d, J=11.3 Hz, 1H), 5.33-5.27 (m, 1H), 4.54 (td, J=9.1 Hz, J=5.3 Hz, 1H), 3.31 (d, J=7.2 Hz, 2H), 3.27 (dd, J=14.4 Hz, J=11.0 Hz, 1H), 3.19 (dd, J=14.4 Hz, J=2.9 Hz, 1H), 2.84 (dt, J=15.3 Hz, J=6.6 Hz, 1H), 2.66 (dt, J=15.3 Hz, J=6.5 Hz, 1H), 2.43 (dd, J=13.5 Hz, J=11.3 Hz, 1H), 2.41 (s, 6H), 2.25 (d, J=13.5 Hz, 1H), 2.06-1.99 (m, 3H), 2.04 (s, 3H), 1.95 (s, 3H), 1.83 (s, 3H), 1.80 (s, 3H), 1.74-1.67 (m, 1H), 1.29 (d, J=6.3 Hz, 3H). HRMS (ESI$^+$): Calcd. For $C_{32}H_{46}N_3O_5S$ ([M+H]$^+$), 584.3158. Found: 584.3137.

Example 3

The Preparation of a Representative Pateamine a Carbamate Derivative

In this example, the preparation of a representative pateamine A carbamate derivative of the invention, tert-Butyl ((1$^2$Z,3S,6Z,8E,11S,14S)-3-((1E,3E,5E)-7-(dimethylamino)-2,5-dimethylhepta-1,3,5-trien-1-yl)-9,11-dimethyl- 5,13-dioxo-4,12-dioxa-1(2,4)-thiazolacycloheptadec-aphane-6,8-dien-14-yl) carbamate (MZ578), is described.

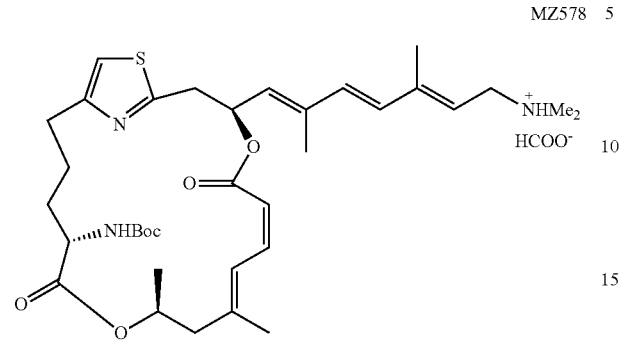

MZ578 tert-Butyl ((1²Z,3S,6Z,8E,11S,14S)-3-((1E,3E,5E)-7-(dimethylamino)-2,5-dimethylhepta-1,3,5-trien-1-yl)-9,11-dimethyl-5,13-dioxo-4,12-dioxa-1(2,4)-thiazolacycloheptade-caphane-6,8-dien-14-yl) carbamate (MZ578). The coupling between MZ554 (6.2 mg, 0.0104 mmol, 1 equiv.) and Fragment G (8.6 mg, 0.0207 mmol, 2 equiv.) followed the known procedure. Low, W. K., Li, J., Zhu, M., Kommaraju, S. S., Shah-Mittal, J., Hull, K., Liu, J. O., and Romo, D. (2014) Second-generation derivatives of the eukaryotic translation initiation inhibitor pateamine A targeting eIF4 Å as potential anticancer agents, Bioorg. Med. Chem. 22, 116-125. The desired product was obtained in the form of salt with formic acid as a colorless oil (4.8 mg, 67%) after purification by prep-HPLC using the same conditions as MZ576. $^1$H NMR (500 MHz, CDCl$_3$) δ 8.52 (brs, 1H), 6.96 (d, J=11.7 Hz, 1H), 6.80 (s, 1H), 6.68 (t, J=11.7 Hz, 1H), 6.38 (d, J=15.8 Hz, 1H), 6.30 (d, J=15.8 Hz, 1H), 6.27 (ddd, J=10.8 Hz, J=9.0 Hz, J=3.4 Hz, 1H), 5.66 (t, J=7.4 Hz, 1H), 5.62 (d, J=8.8 Hz, 1H), 5.48 (d, J=11.5 Hz, 1H), 5.31-5.24 (m, 1H), 4.95 (d, J=8.8 Hz, 1H), 4.23-4.17 (m, 1H), 3.43 (d, J=7.6 Hz, 2H), 3.25 (dd, J=14.5 Hz, J=10.6 Hz, 1H), 3.19 (dd, J=14.5 Hz, J=3.5 Hz, 1H), 2.88-2.82 (m, 1H), 2.71-2.66 (m, 1H), 2.49 (s, 6H), 2.41 (dd, J=13.8 Hz, J=11.3 Hz, 1H), 2.23 (d, J=13.8 Hz, 1H), 1.96 (s, 3H), 1.92-1.87 (m, 3H), 1.86 (s, 3H), 1.80 (s, 3H), 1.74-1.67 (m, 1H), 1.45 (s, 9H), 1.29 (d, J=6.3 Hz, 3H). HRMS (ESI$^+$): Calcd. For C$_{35}$H$_{52}$N$_3$O$_6$S ([M+H]$^+$), 642.3577. Found: 642.3496.

Example 4

The Preparation of a Representative Pateamine A Sulfonamide Derivative

In this example, the preparation of a representative pateamine A sulfonamide derivative of the invention, N-((1²Z,3S,6Z,8E,11S,14S)-3-((1E,3E,5E)-7-(dimethylamino)-2,5-dimethylhepta-1,3,5-trien-1-yl)-9,11-dimethyl-5,13-dioxo-4,12-dioxa-1(2,4)-thiazolacycloheptade-caphane-6,8-dien-14-yl) methyl sulfonamide (MZ624), is described.

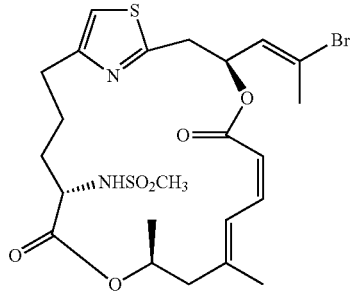

MZ622

N-((1²Z,3S,6Z,8E,11S,14S)-3-((E)-2-bromoprop-1-en-1-yl)-9,11-dimethyl-5,13-dioxo-4,12-dioxa-1(2,4)-thiazolacy-cloheptadecaphane-6,8-dien-14-yl)methanesulfonamide (MZ622). A solution of MZ565 (4.0 mg, 0.0068 mmol, 1 equiv.) in 3 mL of methanol passed through an amino cartridge (BAKERBOND Spe™ Amino Disposable Extraction Column, 500 mg) which was pre-equilibrated with 5 mL of methanol. The cartridge was washed with another 3 mL of methanol. The combined solutions were concentrated, to which were added CH$_2$Cl$_2$ (0.4 mL), pyridine (0.2 mL) and Ms$_2$O (6.0 mg, 0.034 mmol, 5 equiv.) at 0° C. The yellow solution was stirred at 20° C. for 2 hours and concentrated. The residue was purified by a flash chromatography (hexanes:EtOAc=3:1) to afford MZ622 as a yellow oil (3.2 mg, 49%). $^1$H NMR (500 MHz, CDCl$_3$) δ 6.97 (d, J=11.9 Hz, 1H), 6.79 (s, 1H), 6.68 (t, J=11.6 Hz, 1H), 6.32 (ddd, J=9.4 Hz, J=7.9 Hz, J=6.2 Hz, 1H), 5.99 (dq, J=9.3 Hz, J=1.2 Hz, 1H), 5.44 (d, J=11.5 Hz, 1H), 5.29-5.23 (m, 1H), 4.71 (d, J=9.9 Hz, 1H), 3.97 (td, J=10.4 Hz, J=4.0 Hz, 1H), 3.24-3.18 (m, 2H), 2.92 (s, 3H), 2.90-2.78 (m, 2H), 2.43 (s, 3H), 2.42 (dd, J=13.5 Hz, J=10.8 Hz, 1H), 2.25 (d, J=13.5 Hz, 1H), 2.02-1.95 (m, 2H), 1.92-1.87 (m, 1H), 1.82 (s, 3H), 1.51-1.46 (m, 1H), 1.31 (d, J=6.3 Hz, 3H). HRMS (ESI$^+$): Calcd. For C$_{23}$H$_{32}$BrN$_2$O$_6$S$_2$ ([M+H]$^+$), 573.0729. Found: 573.0747.

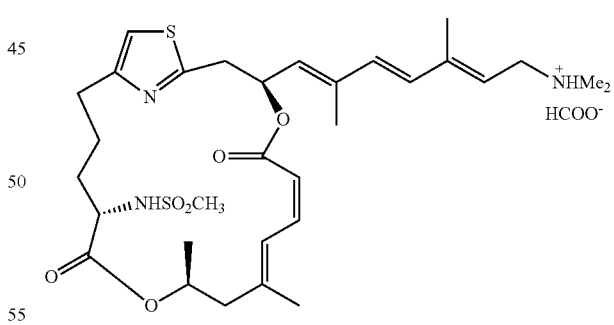

MZ624

N-((1²Z,3S,6Z,8E,11S,14S)-3-((1E,3E,5E)-7-(dimethylamino)-2,5-dimethylhepta-1,3,5-trien-1-yl)-9,11-dimethyl-5,13-dioxo-4,12-dioxa-1(2,4)-thiazolacycloheptade-caphane-6,8-dien-14-yl) methanesulfonamide (MZ624). The coupling between MZ622 (3.0 mg, 0.0052 mmol, 1 equiv.) and Fragment G (4.3 mg, 0.0104 mmol, 2 equiv.) followed the known procedure. Low, W. K., Li, J., Zhu, M., Kommaraju, S. S., Shah-Mittal, J., Hull, K., Liu, J. O., and Romo, D. (2014) Second-generation derivatives of the eukaryotic translation initiation inhibitor pateamine A targeting eIF4 Å as potential anticancer agents, Bioorg. Med.

Chem. 22, 116-125. The purification was the same as for MZ576. The desired product was obtained in the form of salt with formic acid as a colorless oil (2.8 mg, 81%). $^1$H NMR (500 MHz, CDCl$_3$) δ 8.45 (brs, 1H), 6.99 (d, J=11.8 Hz, 1H), 6.81 (s, 1H), 6.67 (t, J=11.6 Hz, 1H), 6.40-6.32 (m, 2H), 6.31 (td, J=9.4 Hz, J=4.3 Hz, 1H), 5.67 (t, J=7.4 Hz, 1H), 5.63 (d, J=9.1 Hz, 1H), 5.47 (d, J=11.4 Hz, 1H), 5.31-5.25 (m, 1H), 4.76 (d, J=9.8 Hz, 1H), 3.98 (td, J=10.2 Hz, J=3.9 Hz, 1H), 3.63-3.60 (m, 2H), 3.26-3.18 (m, 2H), 2.93 (s, 3H), 2.90-2.85 (m, 1H), 2.83-2.76 (m, 1H), 2.62 (s, 6H), 2.43 (dd, J=13.5 Hz, J=11.1 Hz, 1H), 2.25 (d, J=13.5 Hz, 1H), 2.02-1.97 (m, 3H), 1.97 (s, 3H), 1.87 (s, 3H), 1.81 (s, 3H), 1.79-1.72 (m, 1H), 1.31 (d, J=6.3 Hz, 3H). HRMS (ESI$^+$): Calcd. For C$_{31}$H$_{46}$N$_3$O$_6$S$_2$([M+H]$^+$), 620.2828. Found: 620.2855.

Example 5

The Preparation of a Representative Pateamine A Derivatives

In this example, the preparations of representative pateamine A derivatives of the invention, 1,1,1-trichloro-2-methylpropan-2-yl((1$^2$Z,3S,6Z,8E,11S,14R)-3-((1E,3E,5E)-7-(dimethylamino)-2,5-dimethylhepta-1,3,5-trien-1-yl)-9,11-dimethyl-5,13-dioxo-4,12-dioxa-1(2,4)-thiazolacycloheptadecaphane-6,8-dien-14-yl)carbamate (MZ756) and N-((1$^2$Z,3S,6Z,8E,11S,14R)-3-((1E,3E,5E)-7-(dimethylamino)-2,5-dimethylhepta-1,3,5-trien-1-yl)-9,11-dimethyl-5,13-dioxo-4,12-dioxa-1(2,4)-thiazolacycloheptadecaphane-6,8-dien-14-yl) acetamide (MZ757), are described.

2,2,2-Trichloroethyl (R)-2-(tert-butoxycarbonylamino)pent-4-enoate (MZ722)

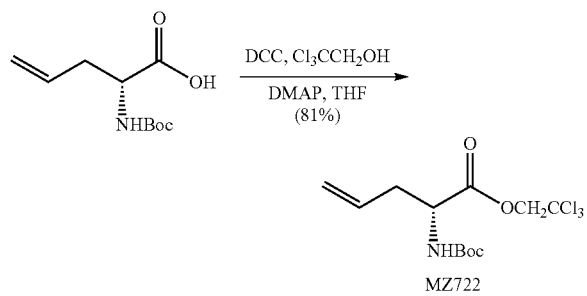

To a solution of (R)-2-(tert-butoxycarbonylamino)pent-4-enoic acid (18.5 g, 86.0 mmol, 1 equiv) in 300 mL of THF at 0° C. were added DMAP (1.05 mg, 8.60 mmol, 0.1 equiv.), DCC (10.9 g, 52.7 mmol, 1.1 equiv.) and 2,2,2-trichloroethanol (8.29 mL, 86.0 mmol, 1 equiv.). The ice bath was removed after 10 minutes and the mixture was stirred at 20° C. under N$_2$ for 24 hours. The suspension was filtered by a sintered Buchner glass funnel and the precipitates were washed with 20 mL of methyl tert-butyl ether. After concentration in vacuo the residue was purified by MPLC (hexanes:ethyl acetate=90:10) to give the product as a colorless oil (24.1 g, 81%). $^1$H NMR (500 MHz, CDCl$_3$) δ 5.74-5.66 (m, 1H), 5.17-5.13 (m, 2H), 5.03 (d, J=7.6 Hz, 1H), 4.88 (d, J=12.0 Hz, 1H), 4.62 (d, J=12.0 Hz, 1H), 4.47 (q, J=6.6 Hz, 1H), 2.63-2.51 (m, 2H), 1.41 (s, 9H). HRMS (ESI$^+$): Calcd. For C$_{12}$H$_{18}$C$_{13}$NO$_4$Na ([M+Na]$^+$), 368.0194. Found: 368.0210.

2,2,2-Trichloroethyl (R,E)-2-(tert-butoxycarbonylamino)-6-oxohept-4-enoate (MZ725)

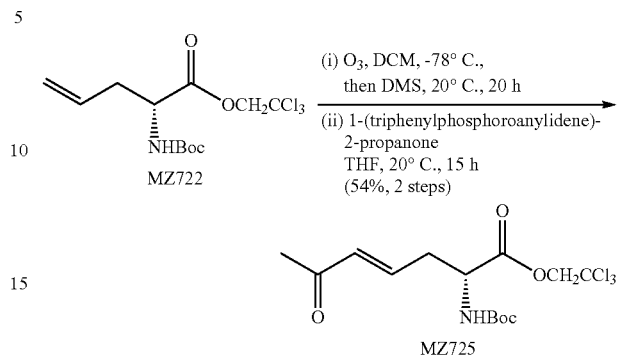

An ozone stream was bubbled through the stirred solution of MZ722 (10.6 g, 30.6 mmol, 1 equiv) in 250 mL of DCM at −78° C. for ca. 10 minutes until the color turned blue. The cold bath was removed and the solution was flushed with N$_2$ for 30 minutes. Dimethyl sulfide (13.8 mL, 187 mmol, 6.1 equiv) was added and the solution was stirred at 20° C. for 20 hours. After concentration 1-(triphenylphosphoranylidene)-2-propanone (19.5 g, 61.2 mmol, 2.0 equiv) and 150 mL of THF was added. The mixture was continued to stir at 20° C. for 15 hours followed by concentration. The residue was purified by MPLC (hexanes:methyl tert-butyl ether=65%:35%) to give the product as a colorless oil (6.4 g, 54%). $^1$H NMR (500 MHz, CDCl$_3$) δ 6.69 (dt, J=15.9 Hz, J=7.3 Hz, 1H), 6.13 (d, J=15.9 Hz, 1H), 5.15 (d, J=7.6 Hz, 1H), 4.91 (d, J=12.0 Hz, 1H), 4.66 (d, J=12.0 Hz, 1H), 4.63-4.59 (m, 1H), 2.87-2.82 (m, 1H), 2.69-2.62 (m, 1H), 2.22 (s, 3H), 1.41 (s, 9H). HRMS (ESI$^+$): Calcd. For C$_{14}$H$_{20}$C$_{13}$NO$_5$Na ([M+Na]$^+$), 410.0299. Found: 410.0317.

(R)-2,2,2-Trichloroethyl 2-(tert-butoxycarbonylamino)-6-oxoheptanoate (MZ728)

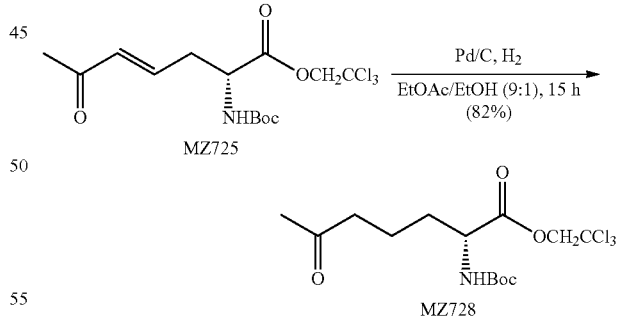

A round-bottom flask was charged with MZ725 (6.30 g, 17.5 mmol, 1 equiv.), Pd/C (10 wt. %, 740 mg, 0.695 mmol, 0.040 equiv.), EtOAc (54 mL), and EtOH (6 mL) followed by setting a H$_2$ balloon on the top of the flask. The mixture was stirred under the H$_2$ atmosphere at 20° C. for 15 hours and then filtered through a short celite pad. The solution was concentrated and the crude residue was purified by MPLC (hexanes:ethyl acetate=70%:30%) to provide the product as a colorless oil (5.20 g, 82%). $^1$H NMR (500 MHz, CDCl$_3$) δ 5.06 (d, J=8.3 Hz, 1H), 4.92 (d, J=11.9 Hz, 1H), 4.65 (d, J=11.9 Hz, 1H), 4.44-4.39 (m, 1H), 2.55-2.43 (m, 2H), 2.13 (s, 3H), 1.92-1.84 (m, 1H), 1.74-1.65 (m, 3H), 1.45 (s, 9H). HRMS (ESI+): Calcd. For $C_{14}H_{22}C_{13}NO_5Na$ ([M+Na]+), 412.0456. Found: 412.0471.

(R)-2,2,2-Trichloroethyl 7-bromo-2-(tert-butoxycarbonylamino)-6-oxoheptanoate (MZ740)

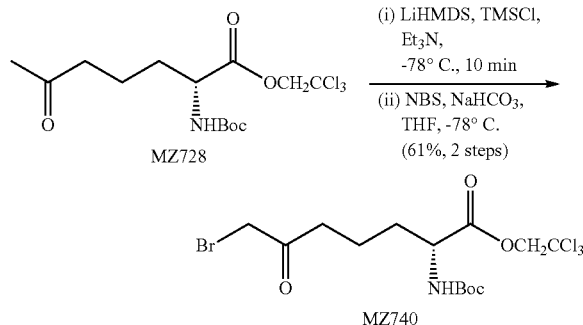

n-Butyllithium solution (2.5 M in THF, 9.28 mL, 23.2 mmol, 3 equiv.) was slowly added to a solution of 1,1,1,3,3,3-hexamethyldisilazane (4.93 mL, 23.2 mmol, 3 equiv.) in 250 mL of THF at −78° C. under $N_2$. The solution was stirred at 0° C. for 20 minutes, cooled to −78° C. and chlorotrimethylsilane (9.90 mL, 77.4 mmol, 10 equiv.) was slowly added followed by MZ442 (3.99 g, 10.65 mmol, 1 equiv.) as a THF solution (20 mL). After 20 minutes anhydrous triethylamine (6.0 mL, 43.2 mmol, 5.6 equiv.) was slowly added. The mixture was continued to stir for 5 minutes and the reaction was quenched with 50 mL of saturated aqueous $NaHCO_3$ solution and extracted with methyl tert-butyl ether (3×100 mL). The organic layer was washed with brine (5 mL), dried over $MgSO_4$ and concentrated in vacuo. The residue was dissolved in 10 mL of THF and the solution was added to a stirred suspension of N-bromosuccinimide (1.38 g, 7.74 mmol, 1.0 equiv.) and $NaHCO_3$ (780 mg, 9.29 mmol, 1.2 equiv.) in THF (100 mL) at −78° C. under $N_2$. After stirring for 1.5 hour, the reaction was quenched by adding 30 mL of saturated aqueous $NaHCO_3$ solution and the mixture was extracted with methyl tert-butyl ether (3×50 mL). The organic layer was washed with brine (5 mL), dried over $MgSO_4$ and concentrated. The crude residue was purified by MPLC (hexanes:ethyl acetate=85%:15%) to provide the product as a yellow oil (2.13 g, 61%). $^1$H NMR (500 MHz, CDCl$_3$) δ 5.05 (d, J=8.3 Hz, 1H), 4.92 (d, J=12.0 Hz, 1H), 4.65 (d, J=12.0 Hz, 1H), 4.46-4.39 (m, 1H), 3.87 (s, 2H), 2.76-2.70 (m, 2H), 1.95-1.89 (m, 1H), 1.80-1.70 (m, 3H), 1.45 (s, 9H). HRMS (ESI): Calcd. For $C_{14}H_{21}BrCl_3NO_5Na$ ([M+Na]+), 489.9561. Found: 489.9575.

2,2,2-Trichloroethyl (R)-5-(2-((R,E)-4-bromo-2-((triisopropylsilyl)oxy)pent-3-en-1-yl)thiazol-4-yl)-2-((tert-butoxycarbonyl)amino)pentanoate (MZ743)

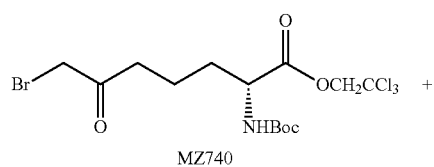

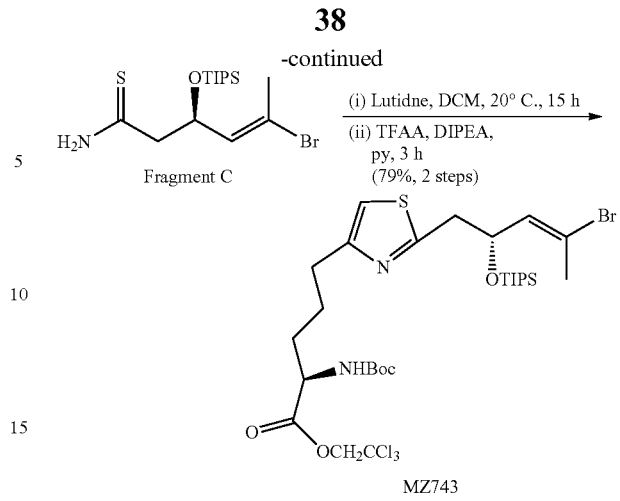

Following the same procedure as in the literature, (Romo, D., Rzasa, R. M., Shea, H. A., Park, K., Langenhan, J. M., Sun, L., Akhiezer, A., and Liu, J. O. (1998) Total Synthesis and Immunosuppressive Activity of (−)-Pateamine A and Related Compounds: Implementation of a β-Lactam-Based Macrocyclization, J. Am. Chem. Soc. 120, 12237-12254) the reaction between MZ740 (2.00 g, 4.26 mmol, 1.1 equiv.) and Fragment C (1.47 g, 3.87 mmol, 1 equiv.) formed the product as a colorless oil (2.24 g, 79%). $^1$H NMR (500 MHz, CDCl$_3$) δ 6.76 (s, 1H), 5.87-5.85 (m, 1H), 5.09 (d, J=8.3 Hz, 1H), 4.92 (d, J=12 Hz, 1H), 4.77 (dt, J=8.9, 6.3 Hz, 1H), 4.63 (d, J=12 Hz, 1H), 4.47-4.42 (m, 1H), 3.22 (dd, J=14.2 Hz, 6.3 Hz, 1H), 3.10 (dd, J=14.2 Hz, 6.4 Hz, 1H), 2.81-2.71 (m, 2H), 2.09 (s, 3H), 1.98-1.92 (m, 1H), 1.86-1.76 (m, 2H), 1.75-1.71 (m, 1H), 1.44 (s, 9H), 1.06-0.97 (m, 21H). HRMS (ESI+): Calcd. For $C_{29}H_{49}BrCl_3N_2O_5SSi$ ([M+H]+), 749.1380. Found: 749.1386.

2,2,2-Trichloroethyl (R)-5-(2-((R,E)-4-bromo-2-hydroxypent-3-en-1-yl)thiazol-4-yl)-2-(tert-butoxycarbonylamino)pentanoate (MZ744)

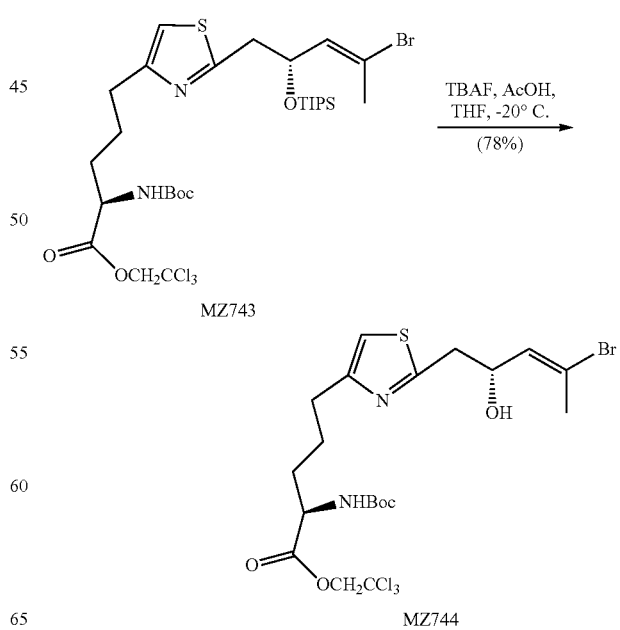

To a solution of MZ743 (2.70 g, 3.59 mmol, 1.0 equiv.) in 180 mL of THF at −20° C. under $N_2$ was added a pre-mixed solution of tetrabutylammonium fluoride (1 M in THF, 10.8 mL, 10.8 mmol, 3 equiv.) and acetic acid (495 μL, 8.63 mmol, 2.4 equiv.) under $N_2$. The mixture was kept in a −20° C. freezer for 15 hours, diluted with 200 mL of methyl tert-butyl ether, washed with saturated aqueous $NaHCO_3$ solution (5 mL), water (5 mL) and brine (5 mL). The organic layer was dried over $MgSO_4$ and concentrated in vacuo. The crude residue was purified by MPLC (hexanes:EtOAc=1:1) to give the product as a colorless oil (1.75 g, 82%). $^1$H NMR (500 MHz, $CDCl_3$) δ 6.78 (s, 1H), 5.95-5.92 (m, 1H), 5.12-5.09 (m, 1H), 4.91 (d, J=12.0 Hz, 1H), 4.73-4.69 (m, 1H), 4.61 (d, J=12.0 Hz, 1H), 4.45-4.41 (m, 1H), 4.23 (brs, 1H), 3.11 (d, J=5.9 Hz, 2H), 2.82-2.72 (m, 2H), 2.27 (s, 3H), 1.95-1.90 (m, 1H), 1.84-1.79 (m, 2H), 1.77-1.70 (m, 1H), 1.43 (s, 9H). HRMS (ESI$^+$): Calcd. For $C_{20}H_{29}BrCl_3N_2O_5S$ ([M+H]$^+$), 593.0046. Found: 593.0051.

(S,E)-4-Bromo-1-(4-((R)-4-(tert-butoxycarbonyl amino)-5-oxo-5-(2,2,2-trichloroethoxy) pentyl)-3λ$^4$-thiazol-2-yl)pent-3-en-2-yl (S,E)-5-methyl-7-(triisopropylsilyloxy)oct-4-en-2-ynoate (MZ747)

Following the same procedure as in the literature, (Romo, D., Choi, N. S., Li, S., Buchler, I., Shi, Z., and Liu, J. O. (2004) Evidence for Separate Binding and Scaffolding Domains in the Immunosuppressive and Antitumor Marine Natural Product, Pateamine A: Design, Synthesis, and Activity Studies Leading to a Potent Simplified Derivative, J. Am. Chem. Soc. 126, 10582-10588.) MZ744 (1.30 g, 2.19 mmol, 1 equiv.) reacted with Fragment F (852 mg, 2.63 mmol, 1.2 equiv.) to afford the product as a colorless oil (1.43 g, 73%). $^1$H NMR (500 MHz, $CDCl_3$) δ 6.80 (s, 1H), 5.89-5.87 (m, 1H), 5.78 (dt, J=9.6 Hz, 6.7 Hz, 1H), 5.41-5.40 (m, 1H), 5.13 (d, J=8.2 Hz, 1H), 4.92 (d, J=12.0 Hz, 1H), 4.63 (d, J=12.0 Hz, 1H), 4.46-4.42 (m, 1H), 4.15-4.09 (m, 1H), 3.38 (dd, J=14.8 Hz, 7.0 Hz, 1H), 3.27 (dd, J=14.8 Hz, 6.4 Hz, 1H), 2.83-2.72 (m, 2H), 2.41 (dd, J=13.2 Hz, 5.3 Hz, 1H), 2.29 (d, J=1.2 Hz, 3H), 2.25 (dd, J=13.2 Hz, 6.9 Hz, 1H), 2.01 (d, J=1.0 Hz, 3H), 1.96-1.91 (m, 1H), 1.86-1.80 (m, 2H), 1.76-1.69 (m, 1H), 1.44 (s, 9H), 1.13 (d, J=6.0 Hz, 3H), 1.05 (s, 21H). HRMS (ESI$^+$): Calcd. For $C_{38}H_{59}BrCl_3N_2O_7SSi$ ([M+H]$^+$), 901.2041. Found: 901.2040.

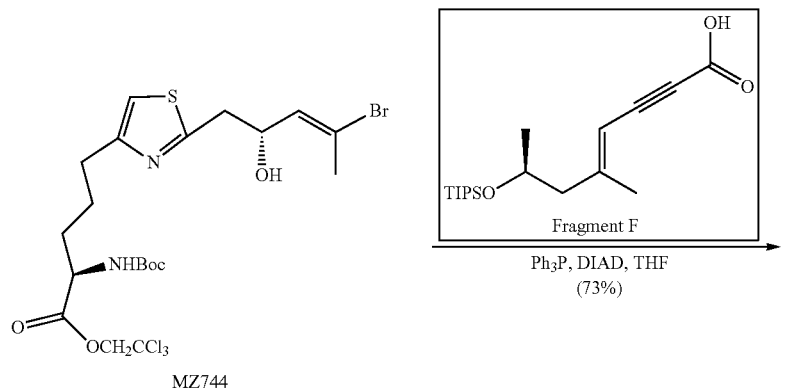

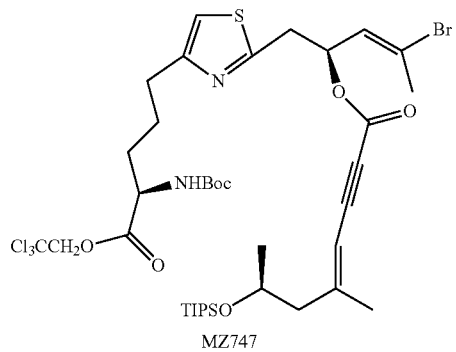

41

(S,E)-4-Bromo-1-(4-((R)-4-(tert-butoxycarbo-
nylamino)-5-oxo-5-(2,2,2-trichloroethoxy)pentyl)
thiazol-2-yl)pent-3-en-2-yl (S,E)-7-hydroxy-5-methyloct-4-en-2-ynoate (MZ533)

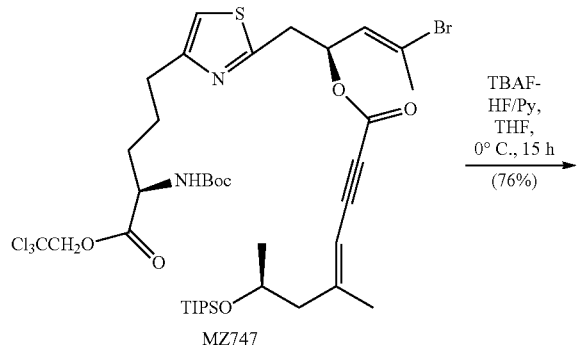

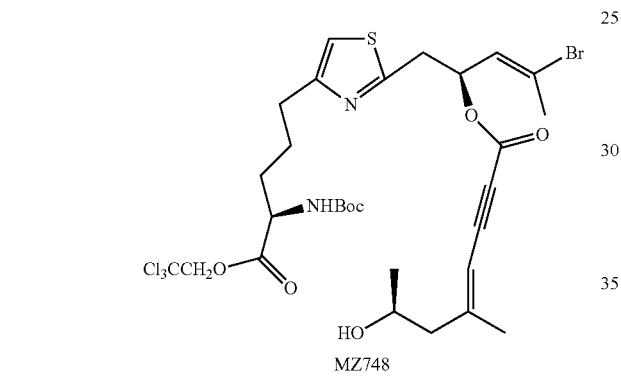

Tetrabutylammonium fluoride (1 M in THF, 5 mL, 5.0 mmol) was mixed with HF/py (70 w/w % HF, 138 µL, 5.3 mmol) at 0° C. and 2.16 mL of the mixture was added to a solution of MZ747 (290 mg, 0.322 mmol) in THF (8.3 mL) at 0° C. The reaction was maintained at 4° C. for 15 hours. The mixture was diluted with 100 mL of EtOAc and was washed with saturated aqueous NaHCO$_3$ solution (5 mL), water (5 mL), and brine (5 mL). The organic layer was dried over MgSO$_4$ and concentrated. The crude residue was purified by MPLC (heaxnes:EtOAc=4:1) to give the desired product as a colorless oil (240 mg, 76%). $^1$H NMR (500 MHz, CDCl$_3$) δ 6.79 (s, 1H), 5.88-5.85 (m, 1H), 5.77 (dt, J=9.7 Hz, 6.3 Hz, 1H), 5.45-5.44 (m, 1H), 5.18 (d, J=8.3 Hz, 1H), 4.90 (d, J=12.0 Hz, 1H), 4.61 (d, J=12.0 Hz, 1H), 4.44-4.40 (m, 1H), 4.02-3.96 (m, 1H), 3.36 (dd, J=14.8 Hz, 7.0 Hz, 1H), 3.27 (dd, J=14.8 Hz, 6.1 Hz, 1H), 2.82-2.71 (m, 2H), 2.32-2.23 (m, 2H), 2.28 (d, J=1.0 Hz, 3H), 2.01 (d, J=0.9 Hz, 3H), 1.96-1.88 (m, 1H), 1.84-1.78 (m, 2H), 1.74-1.67 (m, 1H), 1.42 (s, 9H), 1.20 (d, J=6.2 Hz, 3H). OH not observed. HRMS (ESI$^+$): Calcd. For C$_{29}$H$_{39}$BrCl$_3$N$_2$O$_7$S ([M+H]$^+$), 743.0727. Found: 743.0728.

42

(R)-5-(2-((S,E)-4-Bromo-2-(((S,E)-7-hydroxy-5-methyloct-4-en-2-ynoyl)oxy)pent-3-en-1-yl) thiazol-4-yl)-2-(tert-butoxycarbonylamino)pentanoic acid (MZ749)

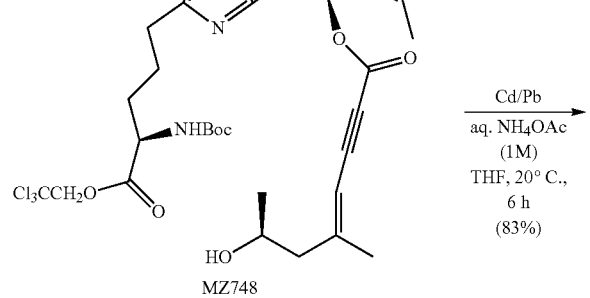

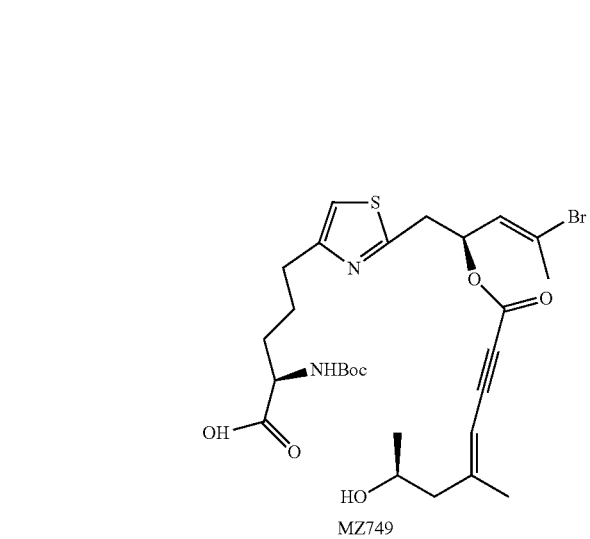

Following the known procedure, (Romo, D., Rzasa, R. M., Shea, H. A., Park, K., Langenhan, J. M., Sun, L., Akhiezer, A., and Liu, J. O. (1998) Total Synthesis and Immunosuppressive Activity of (−)-Pateamine A and Related Compounds: Implementation of a β-Lactam-Based Macrocyclization, J. Am. Chem. Soc. 120, 12237-12254) MZ749 was synthesized from MZ748 (180 mg, 0.242 mmol) as a colorless oil (123 mg, 83%). $^1$H NMR (500 MHz, CDCl$_3$) δ 6.84 (s, 1H), 5.87-5.84 (m, 1H), 5.79-5.74 (m, 1H), 5.44 (s, 1H), 5.31 (d, J=7.8 Hz, 1H), 4.33-4.29 (m, 1H), 4.03-3.97 (m, 1H), 3.39 (dd, J=14.8 Hz, 7.6 Hz, 1H), 3.34 (dd, J=14.8 Hz, 5.9 Hz, 1H), 2.80-2.72 (m, 2H), 2.31-2.24 (m, 2H), 2.27 (d, J=1.2 Hz, 3H), 1.99 (s, 3H), 1.87-1.83 (m, 1H), 1.78-1.69 (m, 3H), 1.42 (s, 9H), 1.21 (d, J=6.2 Hz, 3H). OH not observed. HRMS (ESI$^+$): Calcd. For C$_{27}$H$_{38}$BrN$_2$O$_7$S ([M+H]$^+$), 613.1583. Found: 613.1588.

tert-Butyl ((1²Z,3S,8E,11S,14R)-3-((E)-2-bromoprop-1-en-1-yl)-9,11-dimethyl-5,13-dioxo-4,12-dioxa-1 (2,4)-thiazolacycloheptadecaphane-6-yn-8-en-14-yl)carbamate (MZ750)

tert-Butyl ((1²Z,3S,6Z,8E,11S,14R)-3-((E)-2-bromoprop-1-en-1-yl)-9,11-dimethyl-5,13-dioxo-4,12-dioxa-1 (2,4)-thiazolacycloheptadecaphane-6,8-dien-14-yl)carbamate (MZ751)

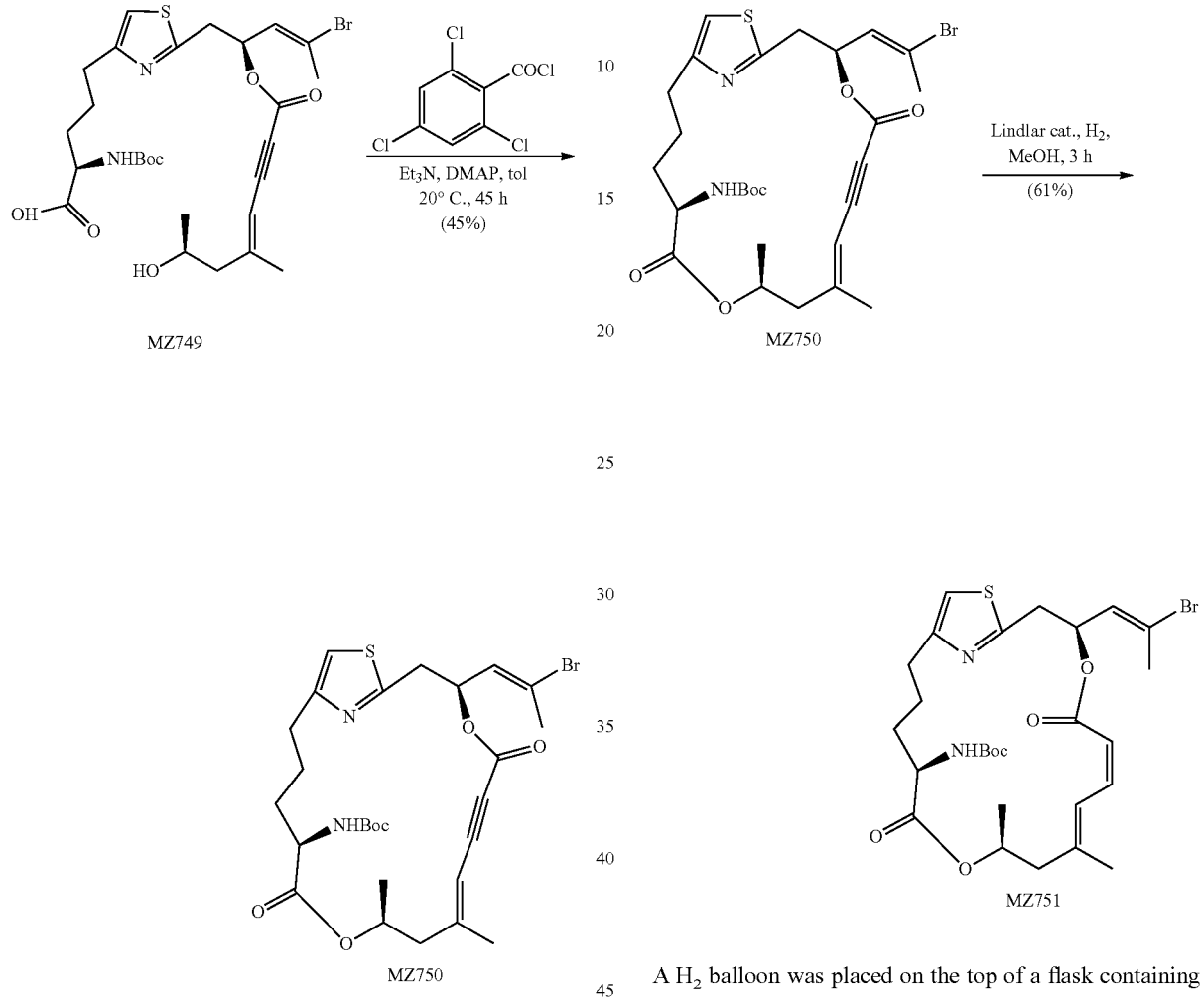

Following the known procedure (Romo, D., Choi, N. S., Li, S., Buchler, I., Shi, Z., and Liu, J. O. (2004) Evidence for Separate Binding and Scaffolding Domains in the Immunosuppressive and Antitumor Marine Natural Product, Pateamine A: Design, Synthesis, and Activity Studies Leading to a Potent Simplified Derivative, J. Am. Chem. Soc. 126, 10582-10588.) but the reaction time was extended to 45 hours, MZ749 (38.0 mg, 0.0619 mmol) afforded the desired product as a colorless oil (17.5 mg, 46%). $^1$H NMR (500 MHz, CDCl$_3$) δ 6.82 (s, 1H), 6.03-6.00 (m, 1H), 5.96-5.91 (m, 1H), 5.33 (s, 1H), 5.26-5.20 (m, 1H), 4.70 (d, J=8.3 Hz, 1H), 4.30-4.26 (m, 1H), 3.33-3.26 (m, 2H), 2.80-2.75 (m, 1H), 2.71-2.66 (m, 1H), 2.43 (d, J=1.3 Hz, 3H), 2.34 (d, J=7.2 Hz, 2H), 1.93-1.87 (m, 1H), 1.89 (s, 3H), 1.72-1.61 (m, 3H), 1.45 (s, 9H), 1.27 (d, J=6.0 Hz, 3H). HRMS (ESI$^+$): Calcd. For C$_{27}$H$_{36}$BrN$_2$O$_6$S ([M+H]$^+$), 595.1477. Found: 595.1483.

A H$_2$ balloon was placed on the top of a flask containing MZ750 (18 mg, 0.030 mmol, 1 equiv.), lindlar catalyst (9.0 mg), and MeOH (2 mL). The mixture was stirred at 20° C. for 3 hours until no starting material visible on TLC and was filtered through a cotton pad which was rinsed with 5 mL of EtOAc. The solvents were evaporated in vacuo and the crude residue was purified on a silica gel chromatography (hexanes:EtOAc=5:1) to provide the product as a colorless oil (11 mg, 61%). $^1$H NMR (500 MHz, CDCl$_3$) δ 6.93 (d, J=11.7 Hz, 1H), 6.71 (t, J=11.7 Hz, 1H), 6.67 (s, 1H), 6.02 (t, J=11.5 Hz, 1H), 5.96 (d, J=9.6 Hz, 1H), 5.72 (d, J=9.7 Hz, 1H), 5.35 (d, J=11.3 Hz, 1H), 5.01-4.95 (m, 1H), 4.16 (t, J=11.1 Hz, 1H), 3.26 (dd, J=14.3 Hz, 2.1 Hz, 1H), 3.14 (dd, J=14.3 Hz, 11.3 Hz, 1H), 2.97-2.93 (m, 1H), 2.59-2.53 (m, 1H), 2.48 (s, 3H), 2.33 (dd, J=12.7 Hz, J=11.1 Hz, 1H), 2.25-2.20 (m, 1H), 2.10 (d, J=12.7 Hz, 1H), 1.81 (s, 3H), 1.73-1.64 (m, 3H), 1.45 (s, 9H), 1.24 (d, J=6.3 Hz, 3H). HRMS (ESI$^+$): Calcd. For C$_{27}$H$_{38}$BrN$_2$O$_6$S ([M+H]$^+$), 597.1634. Found: 597.1637.

45

($1^2$Z,3S,6Z,8E,11S,14R)-14-Amino-3-((E)-2-bromoprop-1-en-1-yl)-9,11-dimethyl-4,12-dioxa-1(2,4)-thiazolacycloheptadecaphane-6,8-diene-5,13-dione (MZ752)

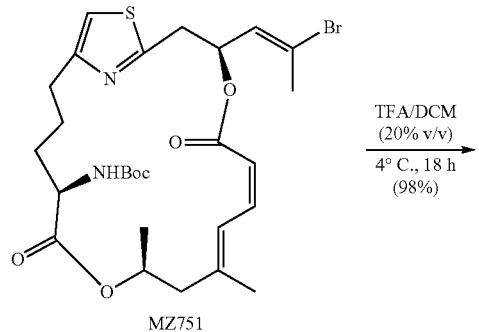

46

1,1,1-Trichloro-2-methylpropan-2-yl (($1^2$Z,3S,6Z,8E,11S,14R)-3-((E)-2-bromoprop-1-en-1-yl)-9,11-dimethyl-5,13-dioxo-4,12-dioxa-1(2,4)-thiazolacycloheptadecaphane-6,8-dien-$1^4$-yl) carbamate (MZ754)

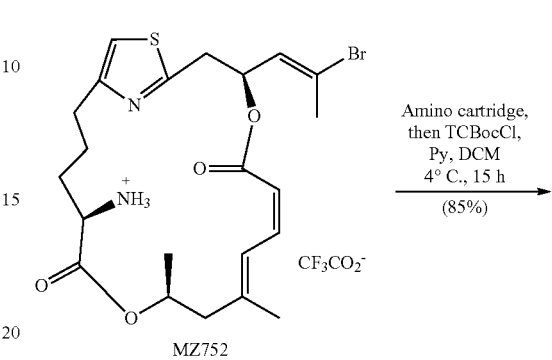

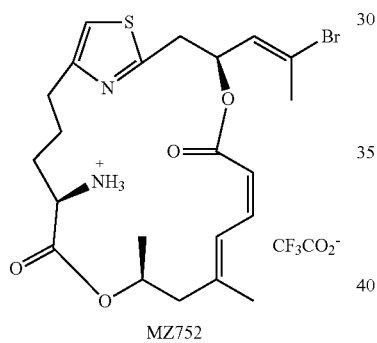

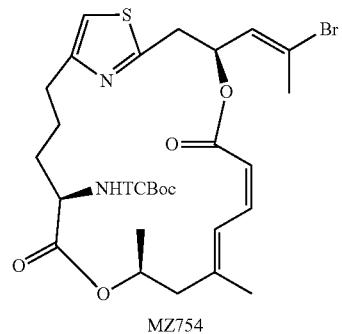

A solution of trifluoroacetic acid (0.3 mL) in DCM (1.5 mL) was cooled to 0° C. and added to MZ554 (12.0 mg, 0.020 mmol) at 0° C. under $N_2$. The reaction was kept in a 4° C. refrigerator for 18 hours. Toluene (10 mL) was added and the solvents were evaporated in vacuo with the water bath was kept at 20° C. The crude residue was purified on a silica gel chromatography (DCM:MeOH=20:1) to give the product as a colorless oil in the form of a TFA salt (12 mg, 98%). $^1$H NMR (500 MHz, $CDCl_3$) δ 6.81 (s, 1H), 6.79 (t, J=11.5 Hz, 1H), 6.72 (s, 1H), 6.2 (td, J=10.1 Hz, 2.8 Hz, 1H), 5.95 (d, J=9.4 Hz, 1H), 5.46 (d, J=9.1 Hz, 1H), 5.14-5.08 (m, 1H), 4.12-4.09 (m, 1H), 3.24 (dd, J=14.9 Hz, 2.8 Hz, 1H), 3.17 (dd, J=14.9 Hz, 10.6 Hz, 1H), 2.91-2.87 (m, 1H), 2.62-2.57 (m, 1H), 2.53 (dd, J=13.1 Hz, 11.2 Hz, 1H), 2.43 (s, 3H), 2.23-2.15 (m, 1H), 2.19 (d, J=13.1 Hz, 1H), 1.89-1.80 (m, 2H), 1.83 (s, 3H), 1.77-1.70 (m, 1H), 1.33 (d, J=6.2 Hz, 3H). $NH_3^+$ not observed. HRMS ($ESI^+$): Calcd. For $C_{22}H_{30}BrN_2O_4S$ ($[M+H]^+$), 497.1110. Found: 497.1122.

Following the known procedure, (Romo, D., Rzasa, R. M., Shea, H. A., Park, K., Langenhan, J. M., Sun, L., Akhiezer, A., and Liu, J. O. (1998) Total Synthesis and Immunosuppressive Activity of (−)-Pateamine A and Related Compounds: Implementation of a β-Lactam-Based Macrocyclization, J. Am. Chem. Soc. 120, 12237-12254) MZ752 (6.7 mg, 0.0014 mmol) afforded the desired product as a colorless oil (8.0 mg, 85%). $^1$H NMR indicates a mixture of rotamers (3:1). The major rotamer: $^1$H NMR (600 MHz, $CDCl_3$) δ 6.83 (d, J=11.7 Hz, 1H), 6.69 (t, J=11.7 Hz, 1H), 6.68 (s, 1H), 6.15-6.11 (m, 1H), 6.03 (d, J=9.8 Hz, 1H), 5.95 (d, J=9.0 Hz, 1H), 5.37 (d, J=11.7 Hz, 1H), 5.00-4.95 (m, 1H), 4.19-4.15 (m, 1H), 3.26 (dd, J=14.3 Hz, 2.7 Hz, 1H), 3.12 (J=14.3 Hz, 11.4 Hz, 1H), 3.01-2.98 (m, 1H), 2.59-2.55 (m, 1H), 2.46 (s, 3H), 2.30 (dd, J=13.1 Hz, 11.2 Hz, 1H), 2.27-2.22 (m, 1H), 2.11 (d, J=13.1 Hz, 1H), 1.95 (s, 6H, $2CH_3$), 1.82 (s, 3H), 1.75-1.64 (m, 3H), 1.25 (d, J=6.2 Hz, 3H). HRMS ($ESI^+$): Calcd. For $C_{27}H_{35}BrCl_3N_2O_6S$ ($[M+H]^+$), 699.0465. Found: 699.0457.

1,1,1-Trichloro-2-methylpropan-2-yl ((1²Z,3S,6Z, 8E,11S,14R)-3-((1E,3E,5E)-7-(dimethylamino)-2,5-dimethylhepta-1,3,5-trien-1-yl)-9,11-dimethyl-5,13-dioxo-4,12-dioxa-1 (2,4)-thiazol acycloheptadecaphane-6,8-dien-14-yl)carbamate (MZ756)

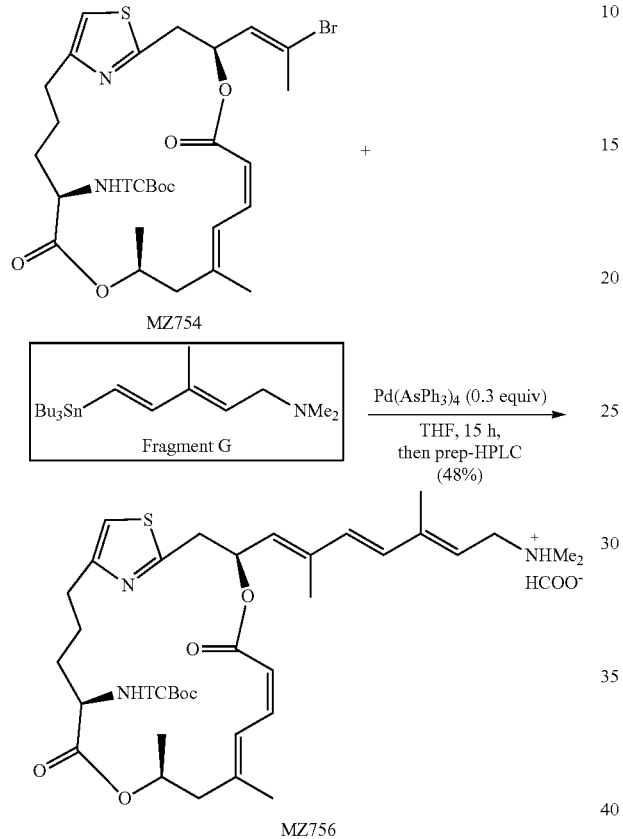

The coupling between MZ754 (2.3 mg, 0.0033 mmol, 1 equiv.) and Fragment G (2.7 mg, 0.0066 mmol, 2 equiv.) followed the known procedure. Low, W. K., Li, J., Zhu, M., Kommaraju, S. S., Shah-Mittal, J., Hull, K., Liu, J. O., and Romo, D. (2014) Second-generation derivatives of the eukaryotic translation initiation inhibitor pateamine A targeting eIF4 Å as potential anticancer agents, Bioorg. Med. Chem. 22, 116-125. The reaction mixture was kept at 20° C. for 15 hours and transferred directly to a silica gel chromatography for purification (dichloromethane:MeOH:triethylamine=50:1:0.1). The product was further purified by the Prep-HPLC (solvent A: H$_2$O buffered with 8 mM HCOOH and 12 mM NH$_3$,H$_2$O, pH=9.0; solvent B: CH$_3$CN/H$_2$O (9:1 v/v) buffered with 8 mM HCOOH and 12 mM NH$_3$,H$_2$O; isocratic elution, solvent A/solvent B=1:4). The collected fractions were concentrated to give a mixture of the product and solid ammonium formate, upon which DCM (10 mL) was added and the suspension was filtered through a sintered Buchner glass funnel. The precipitates were rinsed with extra dichloromethane (2×5 mL). After concentration in vacuo the product was obtained as a colorless oil in the form a salt with formic acid (2.0 mg, 48%). $^1$H NMR indicates a mixture of rotamers (4:1). Major rotamer: $^1$H NMR (600 MHz, CDCl$_3$) δ 8.56 (brs, 1H), 6.83 (d, J=11.6 Hz, 1H), 6.67 (s, 1H), 6.66 (t, J=11.6 Hz, 1H), 6.41 (d, J=15.9 Hz, 1H), 6.35 (ddd, J=11.5 Hz, 8.8 Hz, 2.9 Hz, 1H), 6.26 (d, J=16.0 Hz, 1H), 6.16 (d, J=9.7 Hz, 1H), 5.69 (t, J=7.1 Hz, 1H), 5.55 (d, J=8.5 Hz, 1H), 5.39 (d, J=11.6 Hz, 1H), 4.99-4.95 (m, 1H), 4.19-4.15 (m, 1H), 3.28-3.24 (m, 2H), 3.12 (dd, J=14.1 Hz, 11.4 Hz, 1H), 3.02-2.99 (m, 1H), 2.59-2.54 (m, 1H), 2.39 (s, 6H), 2.32-2.25 (m, 1H), 2.27-2.22 (m, 1H), 2.09 (d, J=12.9 Hz, 1H), 2.01-1.95 (m, 1H), 1.99 (s, 3H), 1.95 (s, 6H, 2CH$_3$), 1.84 (s, 3H), 1.80 (s, 3H), 1.76-1.65 (m, 3H), 1.25 (d, J=6.2 Hz, 3H). HRMS (ESI$^+$): Calcd. For C$_{35}$H$_{49}$C$_{13}$N$_3$O$_6$S ([M+H]$^+$), 744.2408. Found: 744.2338.

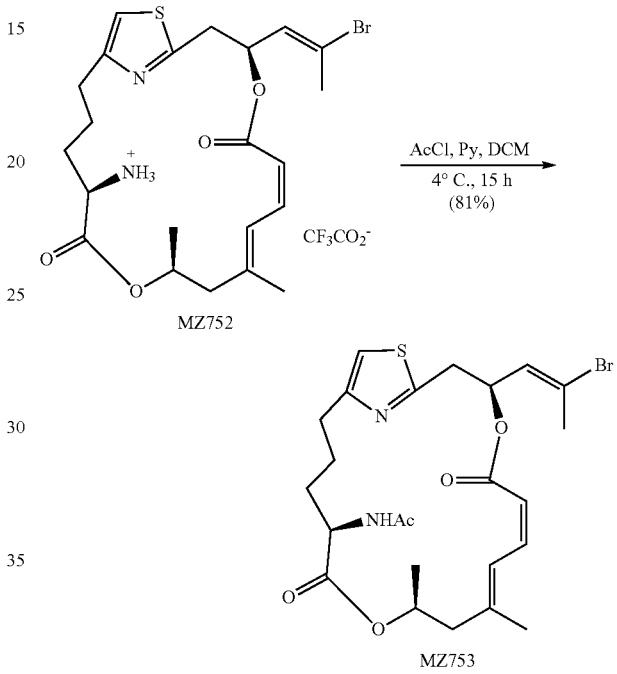

N-((1²Z,3S,6Z,8E,11S,14R)-3-((E)-2-bromoprop-1-en-1-yl)-9,11-dimethyl-5,13-dioxo-4,12-dioxa-1 (2,4)-thiazolacycloheptadecaphane-6,8-dien-14-yl) acetamide (MZ753). To a solution of MZ752 (10.5 mg, 0.015 mmol, 1 equiv.) in 0.5 mL of CH$_2$Cl$_2$ were added pyridine (0.25 mL, excess) and AcCl (6.2 μL, 0.09 mmol, 6 equiv.) at 0° C. The reaction was continued at 4° C. for 15 hours. The mixture was diluted with 25 mL of EtOAc, washed with saturated aq. NaHCO$_3$, H$_2$O and brine. The organic phase was dried over MgSO$_4$ and concentrated in vacuo. The residue was purified by a flash chromatography (hexanes:acetone=2:1) to give the desired product as a colorless oil (7.5 mg, 81%). $^1$H NMR (500 MHz, CDCl$_3$) δ 6.90 (d, J=11.6 Hz, 1H), 6.88 (d, J=8.9 Hz, 1H), 6.76 (t, J=11.6 Hz, 1H), 6.68 (s, 1H), 6.12 (ddd, J=11.1 Hz, 9.7 Hz, 2.8 Hz, 1H), 5.89-5.96 (m, 1H), 5.38 (d, J=11.6 Hz, 1H), 5.00-4.95 (m, 1H), 4.59 (ddd, J=11.9 Hz, 9.4 Hz, 2.3 Hz, 1H), 3.25 (dd, J=14.4 Hz, 2.9 Hz, 1H), 3.16 (dd, J=14.4 Hz, 11.0 Hz, 1H), 2.96-2.92 (m, 1H), 2.57-2.51 (m, 1H), 2.46 (d, J=1.3 Hz, 3H), 2.33 (dd, J=13.2 Hz, 10.9 Hz, 1H), 2.12 (d, J=13.2 Hz, 1H), 2.11 (s, 3H), 1.93-1.87 (m, 1H), 1.85-1.80 (m, 1H), 1.83 (s, 3H), 1.73-1.65 (m, 2H), 1.25 (d, J=6.3 Hz, 3H). HRMS (ESI$^+$): Calcd. For C$_{24}$H$_{32}$BrN$_2$O$_5$S ([M+H]$^+$), 539.1215. Found: 539.1229.

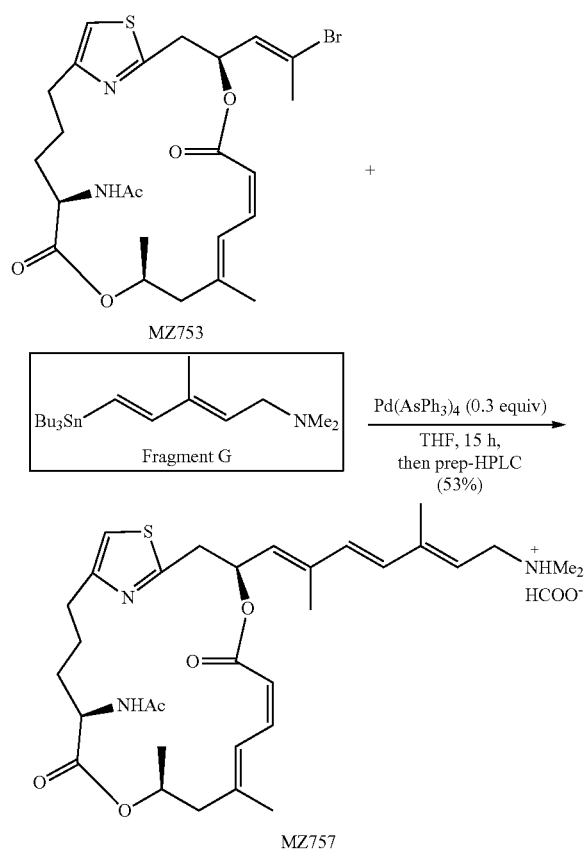

Example 6

Plasma Protein Binding Assay

In this example, a representative plasma protein binding (PPB) assay used to provide the plasma protein binding data is described.

The assay includes the following steps.

1. Frozen plasma was thawed and centrifuged at 1120 g for 10 min to remove any particulates. The plasma was decanted, the pH was measured and, if required, was adjusted to pH7.4 with lactic acid.
2. All compounds were prepared at 10 mM concentration in DMSO. The solutions were carefully vortexed to ensure the compounds dissolved. The 10 mM DMSO solutions were diluted to 500 µM MeOH solutions (5+95 µl).
3. In a 2 mL 96-well plate (DWP), 1000 µL of plasma was pipetted into each well in Columns 1-4.
4. 10 µL of the 500 µM compound solution was pipetted to 1000 µL of corresponding plasma. (The final DMSO=0.05%). The solution was capped and carefully vortexed for 5 min.
5. 200 µL of PBS buffer was added to each receiver well of the dialysis plate (buffer was added to the Receiver first).
6. The bottom of dialysis plate was capped and turned over to the orange donor side (top) of dialysis plate.
7. The orange donor side of the dialysis plate was uncapped and 200 µL of the 10 µM drug/plasma samples were transferred from the 2 ml 96-DWP to the corresponding donor wells in the dialysis plate. The orange donor side of the dialysis plate was then capped.
8. The dialysis plate was placed onto the plate rotator in 37° C. oven and incubated at 37° C. with a rotation speed 20 rpm for 22 hr.
9. To a 1 mL 96-DWP, 50 µL/well of the 5 µM drug/plasma samples was pipetted from the 2 mL 96-DWP in triplicate. 50 µL/well of PBS and then 300 µL of ACN/IS was added. The plate was kept at 4° C. This plate serves as the recovery plate.
10. Two 1 mL 96-DWP were prepared and marked as Donor Plate and Receiver Plate.
11. The dialysis plate was removed from the 37° C. oven.
12. The caps were removed from the donor side of the dialysis plate.
13. 50 µL of samples were pipetted from the donor side of the dialysis plate and added into the 96-DWP Donor Plate. 50 µL of PBS buffer was added into the 96-DWP Donor Plate.
14. The donor side of the dialysis plate was capped and turned over. Caps were removed from the Receiver side wells. 0 uL of samples were pipetted from the Receiver side of the dialysis plate and added to the 96-DWP Receiver Plate.
15. 50 µL of blank plasma was added into the 96-DWP Receiver Plate.
16. 300 µL/well of 1 µM of imipramine (IS) in acetonitrile (ACN) was added into the 96-DWP Donor Plate, the 96-DWP Receiver Plate, and the Recovery Plate.
17. The three plates were capped and vortexed for 10 minutes.
18. The plates were centrifuged at 4° C. at 4000 rpm for 10 min.
19. 150 µL of quench samples were transferred from each plate to a corresponding 96-DWP injection plate.
20. 150 µL of 0.1% acetic acid/water was added to the injection plates.
21. The injection plates were capped and vortexed for 5 min.
22. The plates were centrifuged at 4° C. at 4000 rpm for 5 min.

N-(($1^2$Z,3S,6Z,8E,11S,14R)-3-((1E,3E,5E)-7-(dimethylamino)-2,5-dimethylhepta-1,3,5-trien-1-yl)-9,11-dimethyl-5,13-dioxo-4,12-dioxa-1(2,4)-thiazolacycloheptadecaphane-6,8-dien-14-yl) acetamide (MZ757). The coupling between MZ753 (3.6 mg, 0.0067 mmol, 1 equiv.) and Fragment G (5.5 mg, 0.013 mmol, 2 equiv.) was based on the known procedure. Low, W. K., Li, J., Zhu, M., Kommaraju, S. S., Shah-Mittal, J., Hull, K., Liu, J. O., and Romo, D. (2014) Second-generation derivatives of the eukaryotic translation initiation inhibitor pateamine A targeting eIF4 Å as potential anticancer agents, Bioorg. Med. Chem. 22, 116-125. The purification procedure was the same as that of MZ756, but using a different prep-HPLC condition (solvent A: $H_2O$ buffered with 8 mM HCOOH and 12 mM $NH_3.H_2O$, pH=9.0; solvent B: methanol; gradient elution, solvent A/solvent B=2:3-1:4 within 12 minutes) gave the pure product in the form of salt with formic acid as a colorless oil (2.5 mg, 53%). $^1$H NMR (600 MHz, $CDCl_3$) δ 8.44 (brs, 1H), 6.99 (d, J=9.5 Hz, 1H), 6.91 (d, J=11.6 Hz, 1H), 6.74 (t, J=11.6 Hz, 1H), 6.68 (s, 1H), 6.40 (d, J=15.7 Hz, 1H), 6.35 (ddd, J=11.5 Hz, 9.4 Hz, 3.0 Hz, 1H), 6.33 (d, J=15.7 Hz, 1H), 5.69 (t, J=7.1 Hz, 1H), 5.60 (d, J=9.1 Hz, 1H), 5.40 (d, J=11.6 Hz, 1H), 5.00-4.95 (m, 1H), 4.61 (ddd, J=11.9 Hz, 9.7 Hz, 2.3 Hz, 1H), 3.62 (d, J=7.6 Hz, 2H), 3.25 (dd, J=14.5 Hz, 2.9 Hz, 1H), 3.17 (dd, J=14.5 Hz, J=11.2 Hz, 1H), 2.98-2.94 (m, 1H), 2.62 (s, 6H), 2.57-2.52 (m, 1H), 2.43 (dd, J=13.2 Hz, 10.8 Hz, 1H), 2.16 (s, 3H), 2.14-2.08 (m, 1H), 2.11 (d, J=13.2 Hz, 1H), 2.02 (s, 3H), 1.87 (s, 3H), 1.85-1.80 (m, 1H), 1.82 (s, 3H), 1.72-1.66 (m, 2H), 1.25 (d, J=6.3 Hz, 3H). HRMS (ESI$^+$): Calcd. For $C_{32}H_{46}N_3O_5S$ ([M+H]$^+$), 584.3158. Found: 584.3107.

23. The samples in the Receiver Plate, Donor Plate, and Recovery Plate were analyzed by LC/MS/MS HPLC: Agilent 1290 infinity binary LC/HTC injector. Column: Sigma-Aldrich Supelco Ascentis fused-core C18, 2.7 um, 2.1×20 mm. Solvent A: 0.1% acetic acid/water. Solvent B: 0.1% acetic acid/acetonitrile. Column temperature: 40° C. Injection volume: 2 uL. Time/flow rate: 0 min/0.5 mL/min 11.3 min/0.5 mL/min 11.31 min/1.0 mL/min 11.7 min/1.0 mL/min.

MS/MS: Agilent 6460, Positive, ESI. Sheath gas temperature: 400° C. Sheath gas flow: 12 L/min. Gas temperature: 300° C. Gas flow: 11 L/min. Capillary voltage: 4000 V. Nozzle voltage: 500 V. Nebulizer: 35 psi. Cell accelerator voltage: 7 V.

While the preferred embodiment of the invention has been illustrated and described, it will be appreciated that various changes can be made therein without departing from the spirit and scope of the invention.

The invention claimed is:

1. A compound having the formula:

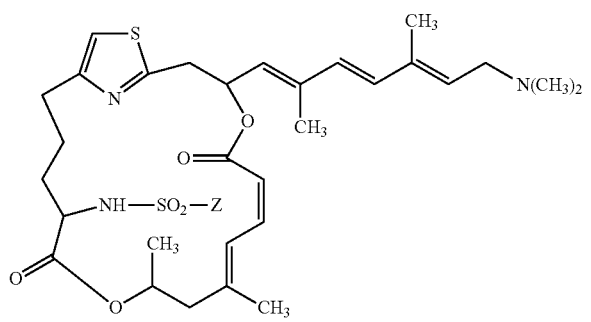

or a stereoisomer, racemate, or a pharmaceutically acceptable salt thereof,
wherein
Z is selected from R and OR',
wherein R is selected from C1-C6 alkyl, C1-C6 haloalkyl, C6-C10 aryl, and C3-C12 alkyl groups in which one or more carbons are replaced with O, NH, or N(CH$_3$), and
wherein R$^1$ is selected from hydrogen, C1-C6 alkyl, C1-C6 haloalkyl, C6-C10 aryl, and C3-C12 alkyl groups in which one or more carbons are replaced with O, NH, or N(CH$_3$).

2. A compound of claim 1 having the formula:

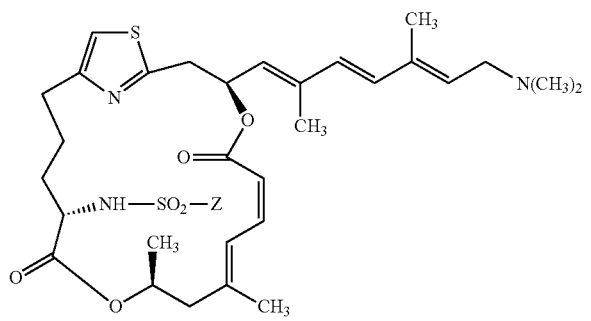

or a pharmaceutically acceptable salt thereof,
wherein
Z is selected from R and OR$^1$,
wherein R is selected from C1-C6 alkyl, C1-C6 haloalkyl, C6-C10 aryl, and C3-C12 alkyl groups in which one or more carbons are replaced with O, NH, or N(CH$_3$), and wherein R$^1$ is selected from hydrogen, C1-C6 alkyl, C1-C6 haloalkyl, C6-C10 aryl, and C3-C12 alkyl groups in which one or more carbons are replaced with O, NH, or N(CH$_3$).

3. The compound of claim 1 having the formula:

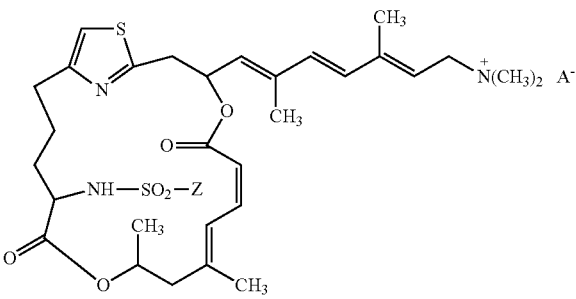

wherein A$^-$ is a pharmaceutically acceptable counter ion.

4. The compound of claim 2 having the formula:

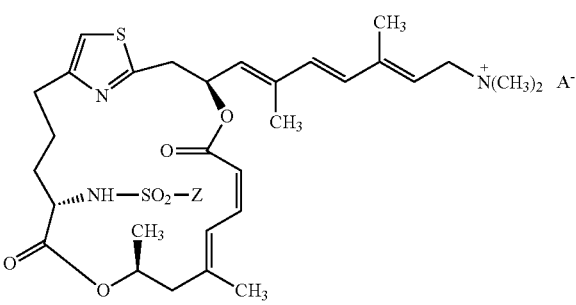

wherein A$^-$ is a pharmaceutically acceptable counter ion.

5. The compound of claim 3, wherein A$^-$ is selected from the group consisting of chloride, bromide, iodide, sulfate, phosphate, formate, acetate, trifluoroacetate, maleate, fumarate, succinate, tartrate, oxalate, citrate, malate, benzoate, toluenesulfonate, methanesulfonate, and benzenesulfonate.

6. The compound of claim 1, wherein Z is C1-C6 alkyl.

7. The compound of claim 1, wherein Z is methyl.

8. The compound of claim 1, wherein Z is C1-C6 haloalkyl.

9. The compound of claim 1, wherein Z is trifluoromethyl.

10. The compound of claim 1, wherein Z is C6-C10 aryl.

11. The compound of claim 1, wherein Z is phenyl.

12. The compound of claim 1, wherein Z is C3-C12 alkyl in which one or more carbons are replaced with O, NH, or N(CH$_3$).

13. The compound of claim 1, wherein Z is selected from CH$_2$—O—CH$_3$, CH$_2$CH$_2$—O—CH$_3$, and —CH$_2$CH$_2$—O—CH$_2$CH$_2$—O—CH$_3$.

14. The compound of claim 1, wherein Z is selected from —CH$_2$—NH—CH$_3$, —CH$_2$—N(CH$_3$)$_2$, —CH$_2$CH$_2$—NH—CH$_3$, and —CH$_2$CH$_2$—N(CH$_3$)$_2$.

15. A pharmaceutical composition, comprising a compound of claim 1, or a stereoisomer or a pharmaceutically acceptable salt thereof, and a pharmaceutically acceptable carrier.

16. An antibody conjugate for the delivery of an α-amino pateamine derivative, comprising a compound of claim 1, or a stereoisomer or a pharmaceutically acceptable salt thereof, covalently coupled directly or through a linker unit to an antibody or functional fragment thereof, wherein the functional fragment is selected from the group consisting of Fab, Fab', F(ab')2, and Fv fragments; linear antibodies; single-chain antibody molecules; an scFv; an IgG ΔCH2, a minibody, a diabody, a triabody, a tetrabody, a dsFv; an sc-Fv-Fc; an (scFv)2; a fragment produced by a Fab expression library; an anti-idiotypic (anti-Id) antibody; and multispecific antibodies formed from antibody fragment(s).

17. A pharmaceutical composition, comprising the antibody conjugate of claim 16 and a pharmaceutically acceptable carrier.

18. A method for inhibiting growth of chronic lymphocytic leukemia (CLL) cells, comprising contacting CLL cells with a compound of claim 1, or a stereoisomer or a pharmaceutically acceptable salt thereof.

19. A method for inhibiting growth of chronic lymphocytic leukemia (CLL) cells, comprising contacting CLL cells with an antibody conjugate of claim 16.

20. A method for treating chronic lymphocytic leukemia (CLL), comprising administering to a subject in need thereof a therapeutically effective amount of a compound of claim 1, or a stereoisomer or a pharmaceutically acceptable salt thereof.

21. A method for treating chronic lymphocytic leukemia (CLL), comprising administering to a subject in need thereof a therapeutically effective amount of a compound an antibody conjugate of claim 16.

* * * * *

UNITED STATES PATENT AND TRADEMARK OFFICE
CERTIFICATE OF CORRECTION

PATENT NO. : 10,870,662 B2  
APPLICATION NO. : 16/555741  
DATED : December 22, 2020  
INVENTOR(S) : Romo et al.

Page 1 of 1

It is certified that error appears in the above-identified patent and that said Letters Patent is hereby corrected as shown below:

In the Claims

| Column | Line | |
|---|---|---|
| 51 | 38 | change "OR'" to -- $OR^1$ -- |
| 52 | 10 | change "$N(CH_3)$" to -- $NH(CH_3)$ -- |
| 52 | 27 | change "$N(CH_3)$" to -- $NH(CH_3)$ -- |
| 52 | 57-58 | change "from CH" to -- from –CH -- |
| 52 | 58 | change "$CH_3, CH_2$" to -- $CH_3,-CH_2$ -- |
| 53 | 30 | change "of a compound an" to -- of an -- |

Signed and Sealed this  
Twenty-ninth Day of March, 2022

Drew Hirshfeld  
*Performing the Functions and Duties of the*  
*Under Secretary of Commerce for Intellectual Property and*  
*Director of the United States Patent and Trademark Office*